(12) United States Patent
Raymond et al.

(10) Patent No.: US 7,511,293 B2
(45) Date of Patent: *Mar. 31, 2009

(54) SCATTEROMETER HAVING A COMPUTER SYSTEM THAT READS DATA FROM SELECTED PIXELS OF THE SENSOR ARRAY

(75) Inventors: Chris Raymond, Bend, OR (US); Steve Hummel, Bend, OR (US)

(73) Assignee: Nanometrics Incorporated, Milpitas, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 11/361,309

(22) Filed: Feb. 24, 2006

(65) Prior Publication Data

US 2006/0278834 A1 Dec. 14, 2006

Related U.S. Application Data

(60) Provisional application No. 60/656,712, filed on Feb. 25, 2005.

(51) Int. Cl.
*G01N 21/86* (2006.01)
(52) U.S. Cl. .................... 250/559.4; 250/208.1
(58) Field of Classification Search ............ 250/559.4, 250/559.44, 548, 216, 208.1, 358.1; 356/601, 356/445, 327.4, 327.5
See application file for complete search history.

(56) References Cited

U.S. PATENT DOCUMENTS

| | | | |
|---|---|---|---|
| 4,428,673 A * | 1/1984 | Yoshida | 359/599 |
| 4,710,642 A | 12/1987 | McNeil | |
| 5,146,213 A | 9/1992 | Brunel et al. | |
| 5,241,369 A | 8/1993 | McNeil et al. | |
| 5,438,414 A | 8/1995 | Rust | |
| 5,703,686 A | 12/1997 | Leroux | |
| 5,703,692 A | 12/1997 | McNeil et al. | |
| 5,771,094 A | 6/1998 | Carter et al. | |
| 5,867,276 A | 2/1999 | McNeil et al. | |

(Continued)

FOREIGN PATENT DOCUMENTS

EP 1 628 164 2/2006

(Continued)

OTHER PUBLICATIONS

Ogawa, Tohru. "Paradigm Shift in Semiconductor Business and Manufacturing." Workshop on Thin Film Metrology—WISE 2000. May 9, 2000. pp. 1-22. XP002390023. Retrieved from the Internet: http://www.eecs.umich.edu/~fredty/wise2000/ogawa.pdf.

(Continued)

*Primary Examiner*—Que T Le
(74) *Attorney, Agent, or Firm*—Silicon Valley Patent Group LLP; Michael J. Halbert

(57) ABSTRACT

Scatterometers and methods of using scatterometry to determine several parameters of periodic microstructures, pseudo-periodic structures, and other very small structures having features sizes as small as 100 nm or less. Several specific embodiments of the present invention are particularly useful in the semiconductor industry to determine the width, depth, line edge roughness, wall angle, film thickness, and many other parameters of the features formed in microprocessors, memory devices, and other semiconductor devices. The scatterometers and methods of the invention, however, are not limited to semiconductor applications and can be applied equally well in other applications.

34 Claims, 8 Drawing Sheets

U.S. PATENT DOCUMENTS

| | | | |
|---|---|---|---|
| 5,880,845 | A | 3/1999 | Leroux |
| 5,889,593 | A | 3/1999 | Bareket |
| 6,137,570 | A | 10/2000 | Chuang et al. |
| 6,429,943 | B1 | 8/2002 | Opsal et al. |
| 6,449,036 | B1 | 9/2002 | Wollmann et al. |
| 6,556,284 | B1 | 4/2003 | Leroux |
| 6,556,290 | B2 | 4/2003 | Maeda et al. |
| 6,734,419 | B1 | 5/2004 | Glenn et al. |
| 6,750,968 | B2 * | 6/2004 | Sandusky .................. 356/369 |
| 6,804,001 | B1 | 10/2004 | Leroux |
| 6,812,045 | B1 | 11/2004 | Nikoonahad et al. |
| 6,890,773 | B1 * | 5/2005 | Stewart ....................... 438/14 |
| 6,895,075 | B2 | 5/2005 | Yokhin et al. |
| 6,940,592 | B2 | 9/2005 | Borden et al. |
| 7,035,375 | B2 | 4/2006 | Yokhin et al. |
| 7,046,376 | B2 * | 5/2006 | Sezginer .................... 356/601 |
| 7,110,099 | B2 | 9/2006 | Littau et al. |
| 2002/0015518 | A1 * | 2/2002 | Matsuoka .................. 382/145 |
| 2002/0035717 | A1 * | 3/2002 | Matsuoka ...................... 716/4 |
| 2002/0039184 | A1 | 4/2002 | Sandusky |
| 2003/0030799 | A1 | 2/2003 | Chen et al. |
| 2003/0071996 | A1 | 4/2003 | Wang et al. |
| 2004/0027477 | A1 | 2/2004 | Tamura et al. |
| 2004/0085537 | A1 | 5/2004 | Ausserre et al. |
| 2004/0246481 | A1 | 12/2004 | Sandusky |
| 2005/0104985 | A1 | 5/2005 | Abe et al. |
| 2006/0126057 | A1 | 6/2006 | Wolf et al. |
| 2006/0148163 | A1 | 7/2006 | Wieczorek et al. |
| 2006/0243912 | A1 | 11/2006 | Raymond et al. |
| 2006/0244969 | A1 | 11/2006 | Ryan et al. |
| 2006/0273263 | A1 | 12/2006 | Raymond et al. |
| 2006/0285110 | A1 | 12/2006 | Raymond et al. |
| 2006/0285111 | A1 | 12/2006 | Raymond et al. |
| 2006/0289788 | A1 | 12/2006 | Raymond et al. |
| 2006/0289789 | A1 | 12/2006 | Raymond et al. |
| 2006/0289790 | A1 | 12/2006 | Raymond et al. |
| 2007/0064247 | A1 | 3/2007 | Petit et al. |

FOREIGN PATENT DOCUMENTS

| | | |
|---|---|---|
| WO | WO 2005/026707 | 3/2005 |
| WO | WO-2006/091781 A1 | 8/2006 |
| WO | WO-2006/091782 A1 | 8/2006 |
| WO | WO-2006/091783 A1 | 8/2006 |
| WO | WO-2006/091840 A2 | 8/2006 |
| WO | WO-2006/091840 A3 | 8/2006 |
| WO | WO-2006/091859 A1 | 8/2006 |
| WO | WO-2006/091913 A1 | 8/2006 |
| WO | WO-2006/093800 A1 | 9/2006 |

OTHER PUBLICATIONS

Office Action dated May 2, 2007, cited in U.S. Appl. No. 11/361,308.
Response to Office Action dated Jun. 8, 2007, cited in U.S. Appl. No. 11/361,308.
Office Action dated Jun. 29, 2007, cited in U.S. Appl. No. 11/371,673.
Office Action dated Nov. 27, 2006, cited in U.S. Appl. No. 11/361,710.
Response to Office Action dated Apr. 27, 2007, cited in U.S. Appl. No. 11/361,710.
Office Action dated Jul. 19, 2007, cited in U.S. Appl. No. 11/361,710.
International Search Report and Written Opinion of the International Searching Authority, Int'l Application No. PCT/US2006/006537, dated Jul. 26, 2006.
International Search Report and Written Opinion of the International Searching Authority, Int'l Application No. PCT/US2006/006538, dated Jun. 22, 2006.
International Search Report and Written Opinion of the International Searching Authority, Int'l Application No. PCT/US2006/006643, dated Jul. 26, 2006.
International Search Report and Written Opinion of the International Searching Authority, Int'l Application No. PCT/US2006/006679, dated Jul. 26, 2006.
International Search Report and Written Opinion of the International Searching Authority, Int'l Application No. PCT/US2006/006536, dated Jul. 28, 2006.
International Search Report and Written Opinion of the International Searching Authority, Int'l Application No. PCT/US2006/006449, dated Aug. 3, 2006.
International Search Report and Written Opinion of the International Searching Authority, Int'l Application No. PCT/US2006/006775, dated Jul. 26, 2006.
Office Action mailed on Nov. 13, 2007 for U.S. Appl. No. 11/361,677, filed Feb. 24, 2006 by Raymond et al., 11 pages.
Office Action mailed on Jun. 29, 2007 for U.S. Appl. No. 11/361,673, filed Feb. 24, 2006 by Raymond et al., 11 pages.
Response to Office Action mailed on Sep. 28, 2007 for U.S. Appl. No. 11/361,673, filed Feb. 24, 2006 by Raymond et al., 11 pages.
Notice of Allowance mailed on Nov. 29, 2007 for U.S. Appl. No. 11/361,673, filed Feb. 24, 2006 by Raymond et al., 9 pages.
Response to Office Action mailed on Nov. 19, 2007 for U.S. Appl. No. 11/361,710, filed Feb. 24, 2006 by Raymond et al., 9 pages.
Office Action mailed on Mar. 9, 2007 for U.S. Appl. No. 11/361,308, filed Feb. 24, 2006 by Raymond et al., 24 pages.
Final Office Action mailed on Sep. 13, 2007 for U.S. Appl. No. 11/361,308, filed Feb. 24, 2006 by Raymond et al., 25 pages.
Office Action mailed on Mar. 11, 2008 for U.S. Appl. No. 11/361,710 filed on Feb. 24, 2006, by Raymond et al., 12 pages.
Office Action mailed on Mar. 4, 2008 for U.S. Appl. No. 11/361,673 filed on Feb. 24, 2006, by Raymond et al., 11 pages.
Communication pursuant to Article 94(3) EPC mailed on Apr. 21, 2008, in EP Application 06 735 920.8, by Raymond et al. (5 pgs).
Office Action mailed on Apr. 15, 2008 for U.S. Appl. No. 11/361,669 filed on Feb. 24, 2006 by Raymond et al. (6 pgs).
Response to Office Action mailed on Jun. 4, 2008 for U.S. Appl. No. 11/361,673 filed on Feb. 24, 2006 by Raymond et al. (10 pgs).
Response to Office Action mailed on Jun. 4, 2008 for U.S. Appl. No. 11/361,710 filed on Feb. 24, 2006 by Raymond et al. (10 pgs).
Final Office Action mailed on Aug. 8, 2008 for U.S. Appl. No. 11/361,710 filed on Feb. 24, 2006 by Raymond et al., 15 pages.

* cited by examiner

NOMINAL PARAMETER SIMULATION

POP IMAGE

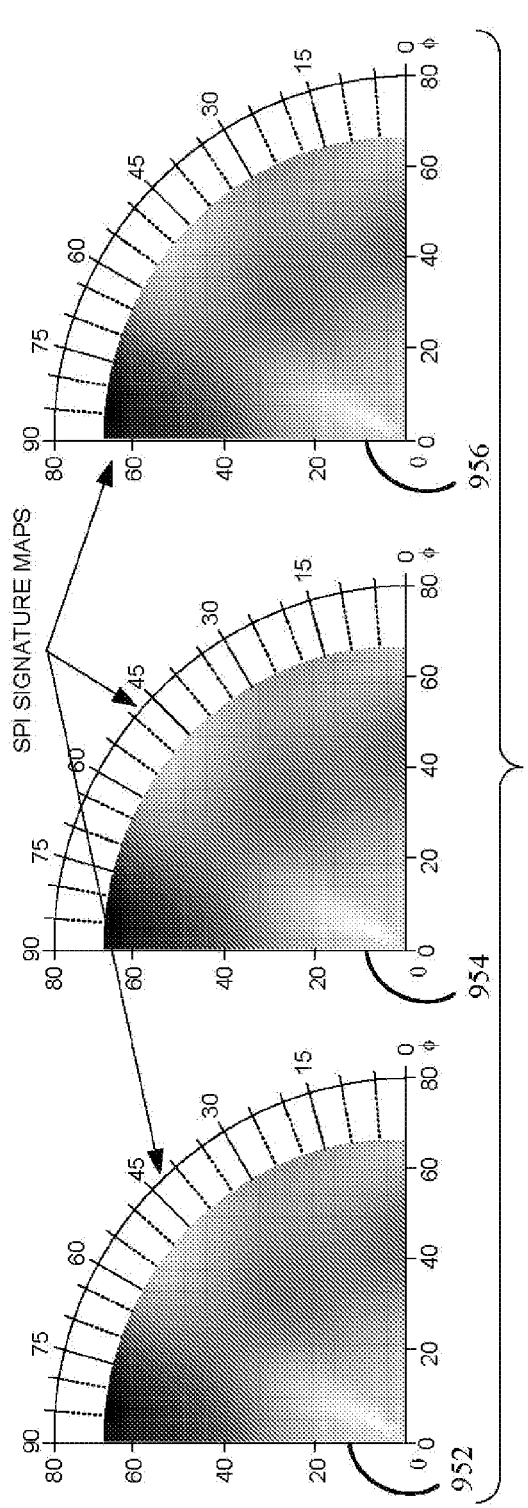
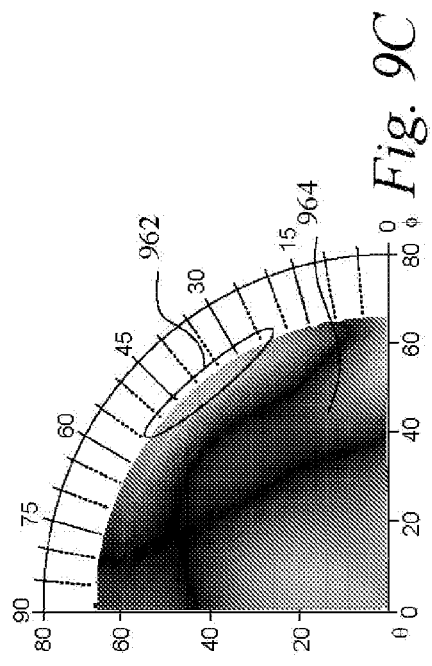
Fig. 9C
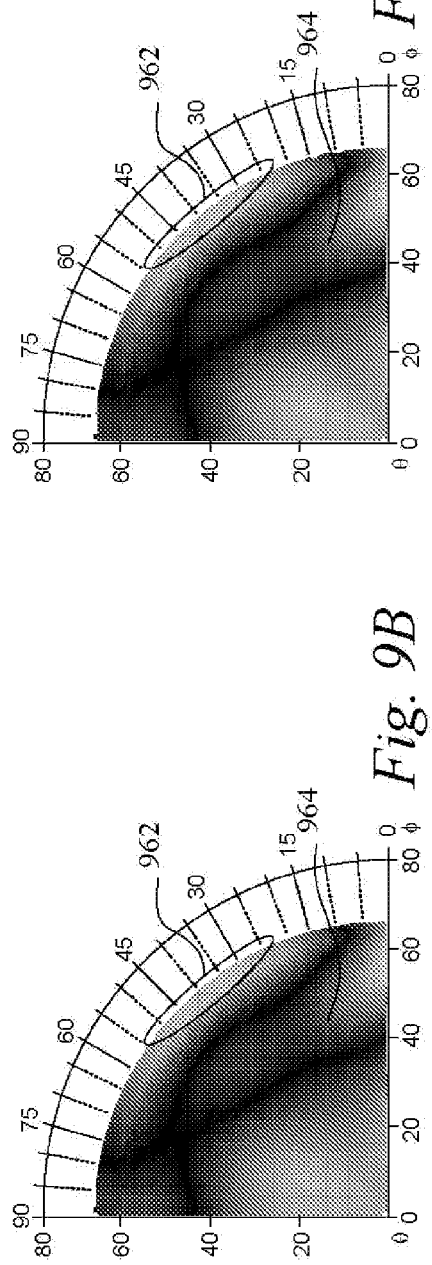
Fig. 9B
Fig. 9A

US 7,511,293 B2

SCATTEROMETER HAVING A COMPUTER SYSTEM THAT READS DATA FROM SELECTED PIXELS OF THE SENSOR ARRAY

CROSS-REFERENCE TO RELATED APPLICATIONS

The present application claims the benefit of U.S. Application No. 60/656,712, filed on Feb. 25, 2005, which is incorporated by reference herein.

TECHNICAL FIELD

The present invention is related to evaluating microstructures on workpieces, such as semiconductor wafers, using apparatus and methods that can obtain a representation of the distribution of radiation returning from the workpiece through a large range of angles of incidence.

BACKGROUND

Semiconductor devices and other microelectronic devices are typically manufactured on a workpiece having a large number of individual dies (e.g., chips). Each wafer undergoes several different procedures to construct the switches, capacitors, conductive interconnects and other components of a device. For example, a workpiece can be processed using lithography, implanting, etching, deposition, planarization, annealing, and other procedures that are repeated to construct a high density of features. One aspect of manufacturing microelectronic devices is evaluating the workpieces to ensure that the microstructures are within the desired specifications.

Scatterometry is one technique for evaluating several parameters of microstructures. With respect to semiconductor devices, scatterometry is used to evaluate film thickness, line spacing, trench depth, trench width, and other aspects of microstructures. Many semiconductor wafers, for example, include gratings in the scribe lanes between the individual dies to provide a periodic structure that can be evaluated using existing scatterometry equipment. One existing scatterometry process includes illuminating such periodic structures on a workpiece and obtaining a representation of the scattered radiation returning from the periodic structure. The representation of return radiation is then analyzed to estimate one or more parameters of the microstructure. Several different scatterometers and methods have been developed for evaluating different aspects of microstructures and/or films on different types of substrates.

Eldim Corporation of France manufactures devices that measure the photometric and colorimetric characteristics of substrates used in flat panel displays and other products. The Eldim devices use an Optical Fourier Transform (OFT) instrument having an illumination source, a beam splitter aligned with the illumination source, and a first lens between the beam splitter and the sample. The first lens focuses the light from the beam splitter to a spot size on the wafer throughout a large range of angles of incidence (e.g., Φ=0° to 360° and Θ=0° to 88°). The light reflects from the sample, and the first lens also focuses the reflected light in another plane. The system further includes an optical relay system to receive the reflected light and a sensor array to image the reflected light. International Publication No. WO 2005/026707 and U.S. Pat. Nos. 6,804,001; 6,556,284; 5,880,845; and 5,703,686 disclose various generations of scatterometers. The scatterometers set forth in these patents are useful for assessing the photometric and colorimetric properties of flat panel displays, but they may have several drawbacks for assessing parameters of extremely small microstructures on microelectronic workpieces.

One challenge of scatterometry is properly locating very small microstructures on a workpiece. This is not particularly difficult for analyzing the pixels of a flat panel display because measuring the photometric and colorimetric properties of such substrates merely requires locating the illumination spot on relatively large pixel areas instead of very small periodic structures. As a result, systems used to analyze flat panel displays may not include navigation systems capable of locating very small microstructures on the order of 20-40 μm. Moreover, the devices used to analyze flat panel displays may have relatively large spot sizes that are not useful to measure the properties of a 20-40 μm grating because such large spot sizes generate reflections from the surrounding areas that result in excessive noise. Therefore, devices designed for assessing flat panel displays may not be well-suited for assessing gratings or other microstructures having much smaller dimensions on microelectronic workpieces.

Another challenge of using scatterometry to evaluate very small microstructures is obtaining a useful representation of the radiation returning from such microstructures. Existing scatterometers that assess the films and surface conditions of flat panel displays typically use relatively long wavelengths of light (e.g., 532 nm). In contrast to flat panel displays, many microstructures on semiconductor wafers have line widths smaller than 70 nm, and such microstructures are continually getting smaller and being packed in higher densities. As a result, the relatively long wavelengths used to assess flat panel displays may not be capable of assessing very small microstructures on many microelectronic devices. Therefore, devices used for assessing flat panel displays may be further inadequate for assessing the properties of microstructures on microelectronic workpieces.

Another challenge of assessing microstructures using scatterometry is processing the data in the representation of the return radiation. Many scatterometers calculate simulated or modeled representations of the return radiation and then use an optimization regression to optimize the fit between the simulated representations and an actual reflectance signal. Such optimization regressions require a significant amount of processing time using high-power computers because the actual reflectance signals for measurements through a large range of incidence angles contain a significant amount of data that is affected by a large number of variables. The computational time, for example, can require several minutes such that the substrates are typically evaluated offline instead of being evaluated in-situ within a process tool. Therefore, many conventional scatterometers may not be well-suited for evaluating microstructures on microelectronic workpieces.

Yet another challenge of assessing microstructures using scatterometry is calibrating the scatterometer. One difficulty of calibrating scatterometers is that the return radiation can have both p- and s-polarized components when the input path is off-axis relative to the microfeature (e.g., a grating). This increases the complexity of fitting the output to a model because the p- and s-polarized components must be treated separately. This is also challenging because the p- and s-polarized components change for each off-axis azimuth angle, and thus proper calibration requires measurements and calculations for several different azimuth angles in more sophisticated applications.

Calibrating scatterometers that operate over a large number of azimuth angles is also difficult because it is challenging to measure the p- and s-polarized components. One existing system for measuring p- and s-polarized components is a two-camera system that splits the output beam into separate p- and s-polarized beams which propagate at a non-parallel angle relative to each other. Such systems have one camera to detect the p-polarized component and another camera to detect the s-polarized component. The use of two cameras, however, is undesirable because the additional camera increases the cost and form factor of the scatterometer. This may prevent such two-camera scatterometers from fitting into many integrated tool sets where metrology is desired. Additionally, it is time-consuming to calibrate two cameras because of the additional camera and compensating for the inherent variations in the cameras. Such two-camera systems are also undesirable because the separate images must be registered and integrated with each other to produce a meaningful result. This is a significant, time-consuming computational procedure. Another system for measuring the p- and s-polarized components uses a single camera and a polarizer that alternates between the p- and s-polarized components. This system may have problems because the serial presentation of the p- and s-polarized components to the detector requires more time to obtain the measurements. Moreover, the polarizer is a mechanical device that moves between p- and s-polarizing states, and as such it may lack the precision and accuracy to obtain meaningful measurements. Such mechanical devices may wear out and further denigrate the precision and accuracy of the calibration. Therefore, obtaining images of p- and s-polarized components for calibrating scatterometers or other uses presents a significant challenge in scatterometry.

Still another challenge of scatterometry is noise or inconsequential data in the measurements. In systems that are able to simultaneously obtain measurements through a large range of altitude and azimuth angles, the data in many areas of the resulting image may not be meaningful. Therefore, there is a need to improve the process of operating scatterometers that simultaneously obtain measurements for a large range of altitude and azimuth angles.

BRIEF DESCRIPTION OF THE DRAWINGS

FIGS. 9A-9C are images illustrating additional aspects of developing a predetermined sensitivity record, acquiring a measured selected radiation distribution, and fitting the measured selected radiation distribution to a modeled selected radiation distribution.

DETAILED DESCRIPTION

A. Overview

Figure 1:
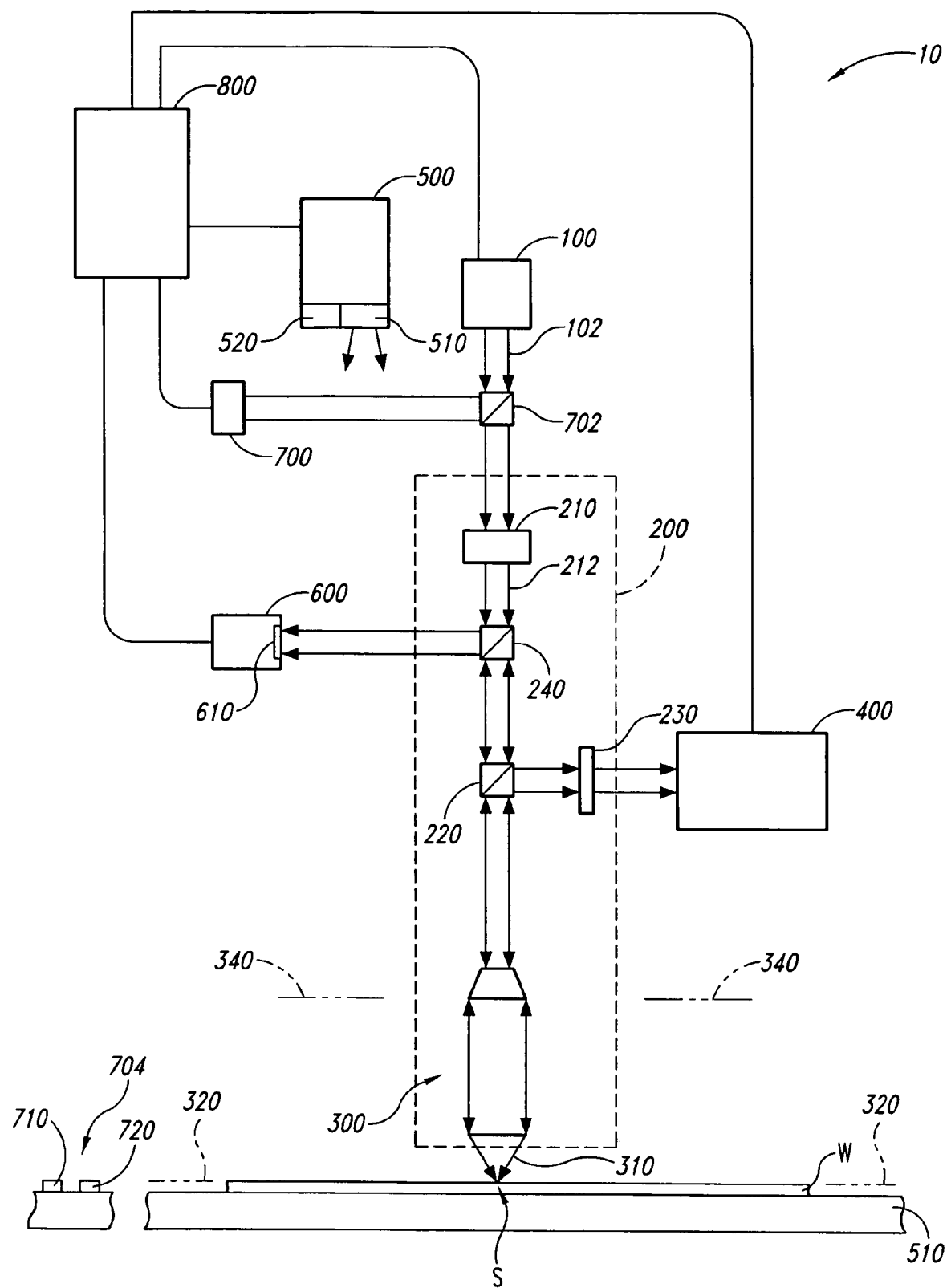
FIG. 1 is a schematic view illustrating a scatterometer in accordance with an embodiment of the invention.

The present invention is directed toward evaluating microstructures on microelectronic workpieces and other types of substrates. Many applications of the present invention are directed toward scatterometers and methods of using scatterometry to determine several parameters of periodic microstructures, pseudo-periodic structures, and other very small structures having features sizes as small as 100 nm or less. Several specific embodiments of the present invention are particularly useful in the semiconductor industry to determine the width, depth, line edge roughness, wall angle, film thickness, and many other parameters of the features formed in microprocessors, memory devices, and other semiconductor devices. The scatterometers and methods of the invention, however, are not limited to semiconductor applications and can be applied equally well in other applications.

One embodiment of the invention is directed toward a scatterometer for evaluating microstructures on workpieces. In this embodiment, the scatterometer comprises an irradiation source, a first optics assembly, and an object lens assembly. The irradiation source can be a laser that produces a first beam of radiation at a wavelength. The first optics assembly is aligned with the path of the beam and configured to condition the beam (e.g., shape, randomize, select order, diffuse, converge, diverge, collimate, etc.), and the object lens assembly is positioned between the first optics assembly and a workpiece site. The object lens assembly is configured to focus the conditioned beam to a spot at an object focal plane. The object lens assembly or another optical assembly of the scatterometer is also configured to (a) receive radiation scattered from a workpiece and (b) present a distribution of the scattered radiation at a second focal plane. For example, the radiation distribution can be the intensity, polarimetric, ellipsometric and/or reflectance distribution of the scattered radiation. The scatterometer of this embodiment can further include a detector, a navigation system, and an auto-focus system. The detector is positioned to receive at least a portion of the radiation distribution and configured to produce a representation of the radiation distribution. The navigation system is operatively coupled to the lens assembly or a support structure holding the workpiece, and it is configured to identify and locate the desired microstructure on the workpiece. The auto-focus system is operatively coupled to one of the lens assembly or the workpiece site, and it is configured to position the microstructure at a desired focal position (e.g., the object focal plane).

Another embodiment of a scatterometer in accordance with the invention comprises a laser configured to produce a beam of radiation having a first wavelength, an optical system having a first optics assembly configured to condition the beam of radiation, and a lens assembly. The lens assembly is configured to focus the beam at an area of an object focal plane or other desired focal plane having a small spot size such that the beam has angles of incidence through a range of altitude angles of at least approximately 0° to 45° and azimuth angles of at least approximately 0° to 90°. The altitude angle ($\Theta$) is the angle between the illumination ray and a reference vector normal to the object focal plane, and the azimuth angle ($\Phi$) is the angle between the incident plane and a reference vector in a plane parallel to the focal plane. The beam more preferably has angles of incidence through altitude angles of 0° to greater than 70° and azimuth angles of 0° to 360°. The scatterometer is further configured to collect and present the radiation scattered from the microstructure at a second focal plane. In one embodiment, the lens assembly itself presents the scattered radiation at the second focal plane, but in other embodiments the optical system has another optic member that presents the radiation distribution at the second focal plane. The scatterometer of this invention further includes a detector positioned to receive the radiation distribution and configured to produce a representation of the radiation distribution. The scatterometer also includes a computer operatively coupled to the detector to receive the representation of the radiation distribution. The computer includes a database and a computer-operable medium. The database has a plurality of simulated radiation distributions corresponding to different sets of parameters of the microstructure. The computer-operable medium contains instructions that cause the computer to identify a simulated radiation distribution that adequately fits the representation of the measured radiation distribution.

Another embodiment of the invention is a scatterometer for evaluating a microstructure on a workpiece comprising an irradiation system, an optical system, and a detector. The irradiation system includes a laser and/or a lamp, and the irradiation system is configured to produce a first beam of radiation having a first wavelength and a second beam of radiation having a second wavelength. The optical system has a first unit configured to condition the first and second beams, and a second unit configured to (a) focus the first and second beams at an area of an object focal plane having a small spot size, and (b) present a distribution of scattered radiation returning from a microstructure at a second focal plane. The detector is positioned to receive the radiation distribution, and the detector is configured to produce a representation of the radiation distribution.

Another embodiment of a scatterometer in accordance with the invention comprises a laser configured to produce a beam of radiation having a wavelength, an optical system, a detector, a calibration unit, and a computer. The optical system has a first optics assembly configured to condition the beam of radiation such that the beam is a diffuse and randomized beam. The optical system also includes an object lens assembly configured to (a) focus the beam at an area of an object focal plane and (b) present scattered radiation returning from a microstructure in a radiation distribution at a second focal plane. The detector is positioned to receive the radiation distribution of the scattered radiation and configured to produce a representation of the radiation distribution. One embodiment of the calibration unit includes a first calibration member having a first reflectivity of the wavelength and a second calibration member having a second reflectivity different than the first reflectivity. The first and second calibration members are located to be irradiated by the beam during a setup procedure to determine a reference reflectance or other reference radiation distribution. In other embodiments, the second calibration unit can be eliminated such that the second reflectance is from free space. The computer is operatively coupled to the detector and includes a computer-operable medium that determines the reference reflectance using a first reflectance from the first calibration member and a second reflectance from the second calibration member or free space.

Still another embodiment of a scatterometer in accordance with the invention comprises a laser and/or lamp configured to produce a beam of radiation having a wavelength and an optical system. The optical system has a first optics assembly including an object lens assembly configured to focus the beam to an area at an object focal plane and present return radiation scattered from a microstructure in a radiation distribution at a second focal plane. The optical system further includes a second optics assembly having a polarizing beam splitter configured to present separate images of p- and s-polarized components of the return radiation. The scatterometer further includes a detector having a single array positioned to simultaneously receive the separate images of the p- and s-polarized components of the return radiation. The detector is also configured to produce a representation of the p- and s-polarized components of the return radiation.

Yet another embodiment of a scatterometer in accordance with the invention comprises a laser and/or lamp configured to produce a beam of radiation having a wavelength and an optical system having a first optics assembly. The first optics assembly includes an object lens assembly configured to focus the beam at an area on an object focal plane and present return radiation scattered from a microstructure in a radiation distribution at a second focal plane. The scatterometer further includes a detector comprising a CMOS imager have a die with an image sensor, focal optics, and packaging that defines an enclosed compartment in which the focal optics and the image sensor are fixed with respect to each other without a cover having parallel, flat surfaces between the image sensor and the focal optics.

The present invention is also directed toward several methods for evaluating a microstructure on a workpiece. One embodiment of such a method comprises generating a laser beam or a beam from a lamp having a wavelength and irradiating a microstructure on a workpiece by passing the beam through a lens assembly that focuses the beam to a focus area at a focal plane. The focus area can have a dimension not greater than 50 μm or in other embodiments approximately at least 10 of the periodic features of the microstructure, and the beam simultaneously has altitude angles of 0° to at least 15° and azimuth angles of 0° to greater than 90°. In several applications, the focus area is not greater than 30 μm, and the altitude angles are 0° to about at least 45°. The altitude angles can be from 0° to at least 70° in other examples. The method further includes detecting an actual radiation distribution corresponding to radiation scattered from the microstructure.

In another embodiment of a method in accordance with the invention the procedure of irradiating a microstructure comprises irradiating the focus area with a laser beam having a first wavelength and irradiating the focus area with a laser beam having a second wavelength different than the first wavelength. The first and second wavelengths can be in a range of approximately 200 nm-475 nm, and more specifically a first wavelength can be from 200 nm-300 nm and a second wavelength can be from 375 nm-475 nm. For example, the first wavelength can be approximately 266 nm and the second wavelength can be approximately 405 nm, or in another embodiment the first wavelength can be about 244 nm and the second wavelength about 457 nm. As such, the workpieces can be irradiated with one or more beams having one or more wavelengths less than 500 nm, but longer wavelengths may be used in other embodiments. In particular, a third wavelength of 633 nm may be used. Another aspect in accordance with another embodiment of the invention includes calibrating the detector by providing a first calibration member having a first reflectivity and a second calibration member having a second reflectivity. The system can be calibrated by determining a reference reflectance using a first reflectance from the first calibration member and a second reflectance from the second calibration member. Other embodiments can use only a single calibration member and obtain a second reflectance measurement from free space.

In yet another embodiment of a method in accordance with the invention, the magnitude and phase of the scattered radiation is measured by the detection system to perform an ellipsometric style measurement described above. The ellipsometric measurement in this embodiment can be performed by positioning polarizers, wave plates, or other phase modifying optical devices in the incident and/or detection optical system assemblies.

In yet another embodiment of a method in accordance with the invention, an automated workpiece transport system is incorporated with the optical system and method to enable automatic high speed measurements across several workpieces without the need for moving or otherwise handling the workpieces manually.

In yet another embodiment of a method in accordance with the invention, the optical system maintains a sine relationship between pixels on the image detector and the altitude illumination angle theta. One example of this relationship is such that displacement, x, in the image plane corresponds to angle $\Theta$ so that $x = F \sin \Theta$, where F is some constant. The advantage to this implementation is that an adequate number of pixels can be sampled throughout the entire image plane. More specifically, for critical sampling of the image plane, the sampling frequency should be twice the highest spatial frequency in the plane. If the highest spatial frequency does not depend on the position in the image plane, then the number of pixels to be averaged (to effectively make a larger pixel of the correct dimensions for critical sampling) does not depend on the position in the image plane. For any other distribution, the number of pixels required to be averaged will depend on position. Thus, unless a sine relationship or another suitable relationship between the pixels on the image sensor and the altitude angle is maintained, then the fixed number of pixels available could result in some regions of the image plane being sampled with fewer than the optimal number of pixels.

Various embodiments of the invention are described in this section to provide specific details for a thorough understanding and enabling description of these embodiments. A person skilled in the art, however, will understand that the invention may be practiced without several of these details or additional details can be added to the invention. Well-known structures and functions have not been shown or described in detail to avoid unnecessarily obscuring the description of the embodiments of the invention. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of items in the list.

B. Embodiments of Scatterometers and Methods for Evaluating Microstructures on Workpieces FIG. 1 is a schematic illustration of a scatterometer 10 in accordance with an embodiment of the invention. In this embodiment, the scatterometer 10 includes an irradiation source 100 that generates a beam 102 at a desired wavelength. The irradiation source 100 can be a laser system and/or lamp capable of producing (a) a beam 102 at a single wavelength, (b) a plurality of beams at different wavelengths, or (c) any other output having a single wavelength or a plurality of wavelengths. In many applications directed toward assessing microstructures on semiconductor workpieces, the irradiation source 100 is a laser that produces a beam having a wavelength less than 500 nm, and more preferably in the range of approximately 266 nm-475 nm. For example, the wavelength can be about 375 nm-475 nm, or in some specific examples about 405 nm or 457 nm. In a different embodiment, the irradiation source 100 can include a plurality of different lasers and/or filters to produce a first beam having a first wavelength of approximately 266 nm and a second beam having a second wavelength of approximately 405 nm, or in another embodiment the first beam can have a wavelength of 405 nm and the second beam can have a wavelength of 457 nm. It will be appreciated that the irradiation source 100 can produce additional wavelengths having shorter or longer wavelengths in the UV spectrum, visible spectrum, and/or other suitable spectrum. The irradiation source 100 can further include a fiber optic cable to transmit the beam 102 through a portion of the apparatus.

The scatterometer 10 further includes an optical system 200 between the irradiation source 100 and a workpiece W. In one embodiment, the optical system 200 includes a first optics assembly 210 that conditions the beam 102 to form a conditioned beam 212. The first optics assembly 210, for example, can include a beam diffuser/randomizer that diffuses and randomizes the radiation to reduce or eliminate the coherence of the beam 102. The first optics assembly 210 can also include a beam element that shapes the beam to have a desired cross-sectional dimension, shape, and/or convergence-divergence. The beam element, for example, can shape the beam 212 to have a circular, rectilinear, or other suitable cross-sectional shape for presentation to additional optic elements downstream from the first optics assembly 210.

The optical system 200 can further include an object lens assembly 300 that focuses the conditioned beam 212 for presentation to the workpiece W and receives radiation reflected from the workpiece W. The object lens assembly 300 is configured to receive the conditioned beam 212 and form a convergent beam 310 focused at a discrete focus area S on a desired focal plane, such as an object focal plane 320. The convergent beam 310 can have a conical shape when the conditioned beam 212 has a circular cross-section, but in other embodiments the convergent beam 310 can have other shapes. For example, when the conditioned beam 212 has a rectilinear cross-section, the convergent beam 310 has a pyramidal shape. As explained in more detail below with reference to Section C, the convergent beam 310 can have a range of incidence angles having altitude angles of 0° to greater than approximately 70° and azimuth angles of 0° to greater than 90° and more preferably 0-360°. The altitude angle is the angle between an incident ray and a reference vector normal to the object focal plane 320, and the azimuth angle is the angle between an incident plane and a reference vector in a plane parallel to the object focal plane 320. The large range of incidence angles generates a large number of unique data points that enable accurate evaluations of several parameters of the microstructure.

The focus area at the object focal plane 320 preferably has a size and shape suitable for evaluating the particular microstructure. For example, when the microstructure is a grating or other structure on a workpiece having a maximum dimension of approximately 10-40 µm, then the focus area is also approximately 10-40 µm. The size of the focal area is preferably not greater than the size of the microstructure so that the radiation does not reflect from features outside of the particular microstructure. In many applications, therefore, the object lens assembly 300 is configured to produce a spot size generally less than 40 µm, and more preferably not greater than 30 µm. The scatterometer 10 can have larger focus areas in other embodiments directed to assessing larger structures.

The object lens assembly 300 is further configured to collect the scattered radiation reflecting or otherwise returning from the workpiece W and present the scattered radiation on a second focal plane 340. The object lens assembly 300, more particularly, presents the scattered radiation in a manner that provides a radiation distribution of the scattered radiation at the second focal plane 340. In one embodiment, the object lens assembly 300 directs the scattered radiation coming at particular angles from the object focal plane 320 to corresponding points on the second focal plane 340. Additional aspects of specific embodiments of the object lens assembly 300 are further described below with reference to Section C.

The optical system 200 can further include a beam splitter 220 through which the conditioned beam 212 can pass to the object lens assembly 300 and from which a portion of the return beam propagating away from the second focal plane 340 is split and redirected. The optical system 200 can optionally include a second optics assembly 230 that receives the split portion of the return beam from the beam splitter 220. The second optics assembly 230 is configured to prepare the return beam for imaging by an imaging device. Additional aspects of specific embodiments of the second optics assembly 230 are described below with reference to Section C.

The scatterometer 10 further includes a detector 400 positioned to receive the radiation distribution propagating back from the second focal plane 340. The detector 400 can be a CCD array, CMOS imager, other suitable cameras, or other suitable energy sensors for accurately measuring the radiation distribution. The detector 400 is further configured to provide or otherwise generate a representation of the radiation distribution. For example, the representation of the radiation distribution can be data stored in a database, an image suitable for representation on a display, or other suitable characterizations of the radiation distribution. Several embodiments of the detector 400 are described below in greater detail with reference to Section D.

The scatterometer 10 can further include a navigation system 500 and an auto-focus system 600. The navigation system 500 can include a light source 510 that illuminates a portion of the workpiece W and optics 520 that view the workpiece W. As explained in more detail below, the navigation system 500 can have a low magnification capability for locating the general region of the microstructure on the workpiece (e.g., global alignment), and a high magnification capability for precisely identifying the location of the microstructure. Several embodiments of the navigation system can use the irradiation source 100 and components of the optical system 200. The navigation system 500 provides information to move the object lens assembly 300 and/or a workpiece site 510 to accurately position the focus area of the object lens assembly 300 at the desired microstructure on the workpiece W.

The auto-focus system 600 can include a focus array 610, and the optical system 200 can include an optional beam splitter 240 that directs radiation returning from the workpiece W to the focus array 610. The auto-focus system 600 is operatively coupled to the object lens assembly 300 and/or the workpiece site 510 to accurately position the microstructure on the workpiece W at the object focal plane 320 of the object lens assembly 300 or another plane. As explained in more detail below with reference to Section E, the navigation system 500 and the auto-focus system 600 enable the scatterometer 10 to evaluate extremely small features of very small microstructures on semiconductor devices or other types of microelectronic devices.

The scatterometer 10 further includes a calibration system for monitoring the intensity of the beam 102 and maintaining the accuracy of the other components. The calibration system (a) monitors the intensity, phase, wavelength or other beam property of the beam 102 in real time, (b) provides an accurate reference reflectance for the detector 400 to ensure the accuracy of the scatterometer, and/or (c) provides angular calibration of the system. In one embodiment, the calibration system includes a detector 700 and a beam splitter 702 that directs a portion of the initial beam 102 to the detector 700. The detector 700 monitors changes in the intensity of the beam 102 in real-time to continuously maintain the accuracy of the measured radiation distribution. The detector 700 can also or alternatively measure phase changes or a differential intensity. The calibration system, for example, can use the polarity of the return radiation to calibrate the system.

The calibration system can further include a calibration unit 704 having one or more calibration members for calibrating the detector 400. In one embodiment, the calibration unit 704 includes a first calibration member 710 having a first reflectance of the wavelength of the beam and a second calibration member 720 having a second reflectance of the wavelength of the beam. The first calibration member 710 can have a very high reflectance, and the second calibration member 720 can have a very low reflectance to provide two data points for calibrating the detector 400. In another embodiment, the second calibration member 720 can be eliminated and the second reflectance can be measured from free space.

The scatterometer 10 further includes a computer 800 operatively coupled to several of the components. In one embodiment, the computer 800 is coupled to the irradiation source 100, the detector 400, the navigation system 500, the auto-focus system 600, and the reference detector 700. The computer 800 is programmed to operate the irradiation source 100 to produce at least a first beam having a first wavelength and preferably to also produce a second beam having a second wavelength, as described above. The computer 800 can also control the source 100 to control the output intensity of the beam. The computer 800 further includes modules to operate the navigation system 500 and auto-focus system 600 to accurately position the focus area of the convergent beam 310 at a desired location on the wafer W and in precise focus.

In several embodiments, the computer 800 further includes a computer-operable medium for processing the measured radiation distribution to provide an evaluation of the microstructure on the workpiece W. For example, the computer 800 can include a database having a plurality of simulated radiation distributions corresponding to known parameters of the microstructure. The computer 800 can include computer-operable media to process the measured radiation distribution in conjunction with the database of simulated radiation distributions in a manner that selects the simulated radiation distribution that best fits the measured radiation distribution. Based upon the selected simulated radiation distribution, the computer stores and/or presents the parameters of the microstructure corresponding to those of the simulated radiation distribution, or an extrapolation or interpolation of such parameters. In another embodiment, the computer 800 can scan or otherwise acquire data from pixels of the detector only where there is a high sensitivity to changes in the parameter(s). Such a selective input to the computer reduces the amount of data and increases the quality of the data for processing in the computer 800. Several aspects of the computer 800 and methods for processing the measured radiation distribution are set forth below in greater detail with reference to Section G.

C. Embodiments of Optics and Lens Assemblies

The scatterometer 10 can have several different embodiments of optics assemblies and lens assemblies for optimizing the scatterometer for use with specific types of microstructures. The object lens assembly 300, for example, can be achromatic to accommodate a plurality of beams at different wavelengths, or it can have a plurality of individual assemblies of lenses that are each optimized for a specific wavelength. Such individual lens assemblies can be mounted on a turret that rotates each lens assembly in the path of the beam according to the wavelength of the particular beam, or such lenses may be mounted in separate, fixed positions that correspond to the incident beam paths of the respective wavelengths. In either case, the object lens assembly 300 is useful for applications that use different wavelengths of radiation to obtain information regarding the radiation returning from the workpiece.

The object lens assembly 300 can also include reflective lenses that are useful for laser beams in the UV spectrum. Certain types of glass may filter UV radiation. As such, when the beam has a short wavelength in the UV spectrum, the object lens assembly 300 and other optic members can be formed from reflective materials that reflect the UV radiation. In another embodiment, the first optics assembly 210 or the object lens assembly 300 may have a polarizing lens that polarizes the radiation for the convergent beam 310 (FIG. 1).

Figure 2:
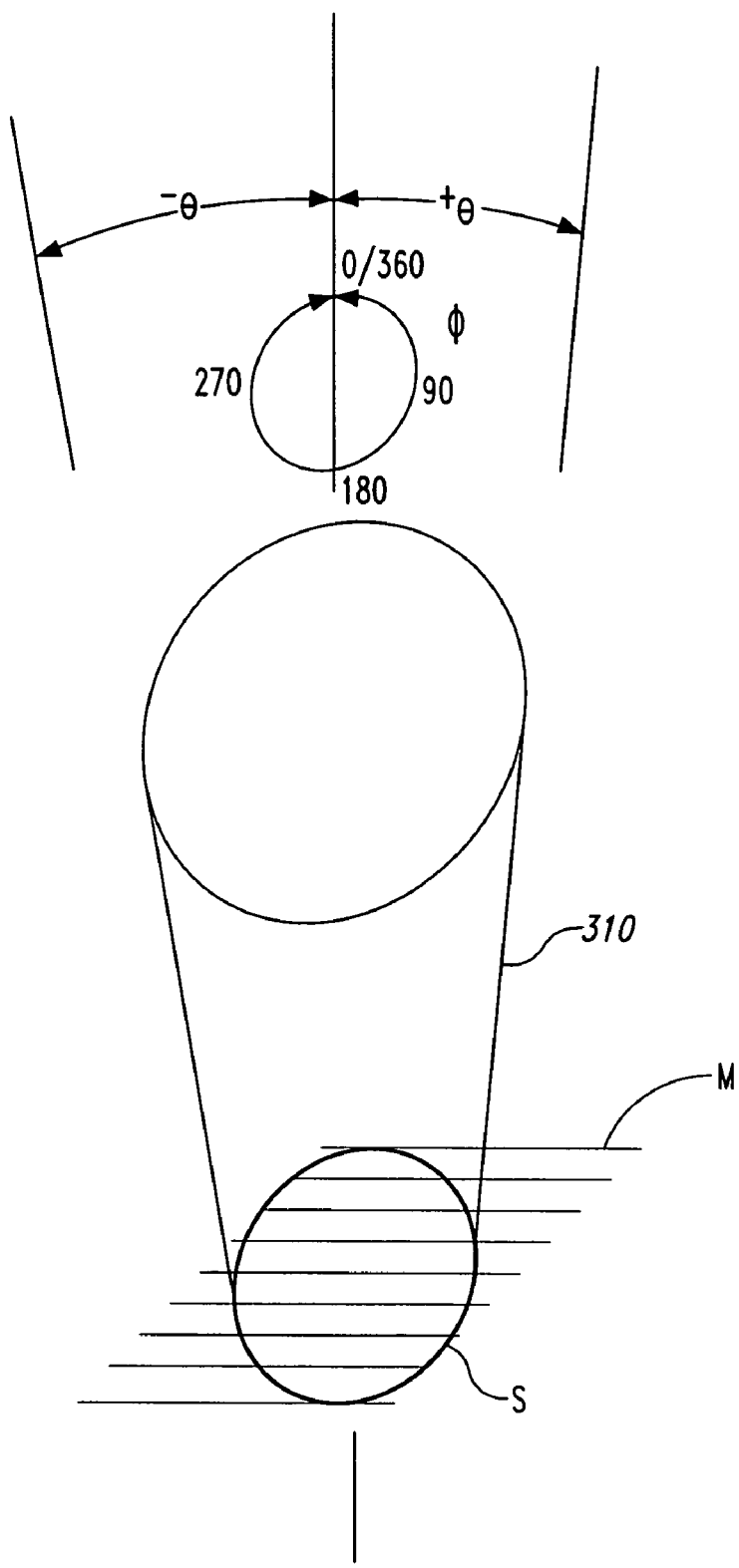
FIG. 2 is a schematic isometric view illustrating a portion of a three-dimensional convergence beam for irradiating microstructures on a workpiece in accordance with an embodiment of the invention.

FIG. 2 illustrates one embodiment of the convergent beam 310 explained above with reference to FIG. 1 formed by an embodiment of the object lens assembly 300. The convergent beam 310 illustrated in FIG. 2 has a frusto-conical configuration that results in a focus area S. The focus area S is smaller than the area of the microstructure under evaluation, but it generally covers at least 8-10 of the periodic structures of the microfeature. In several particular applications for the semiconductor industry, the focus area S is approximately 10-40 µm in diameter, and more preferably approximately 20-30 µm in diameter. The focus area S, however, is not limited to these ranges in other embodiments. The focus area S may not necessarily be circular, and thus the convergent beam 310 is typically configured such that the focus area S has a maximum dimension less than 30 µm (e.g., approximately 50 nm to approximately 30 µm).

The convergent beam 310 simultaneously illuminates a microfeature M through a wide range of incidence angles having large ranges of altitude angles $\Theta$ and azimuth angles $\Phi$. Each incidence angle has an altitude angle $\Theta$ and an azimuth angle $\Phi$. The object lens assembly is generally configured to focus the beam to an area at the object focal plane through at least (a) a 15° range of altitude angles and (b) a 90° range of azimuth angles simultaneously. For example, the incidence angles can be simultaneously focused through altitude angles $\Theta$ of 0° to at least 45°, and more preferably from 0° to greater than 70° (e.g., 0° to 88°), and azimuth angles $\Phi$ of 0° to greater than approximately 90°, and more preferably throughout the entire range of 0° to 360°. As a result, the object lens assembly 300 can form a conical beam having a large range of incidence angles $(\Theta, \Phi)$ to capture a significant amount of data in a single measurement of the workpiece W. This is expected to enhance the utility and throughput of scatterometry for measuring critical dimensions in submicron microstructures in real time and in-situ in a process tool.

Figure 3:
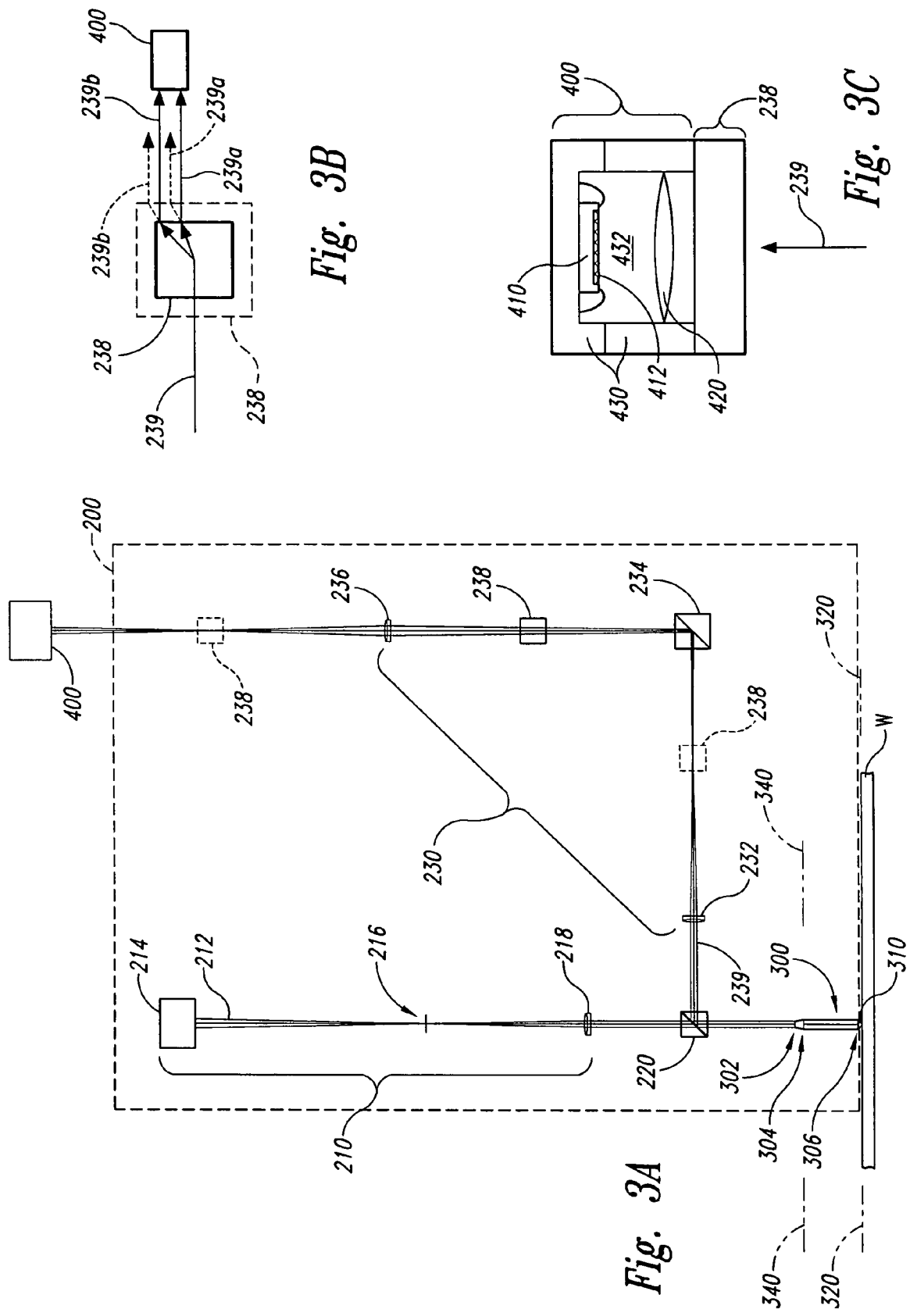
FIG. 3A is a schematic view illustrating an optical system for use in a scatterometer in accordance with an embodiment of the invention.
FIG. 3B is a schematic view of a cube-type polarizing beam splitter for use in a scatterometer in accordance with an embodiment of the invention.
FIG. 3C is a schematic view of a CMOS imager for use in a scatterometer in accordance with an embodiment of the invention.

FIG. 3 is a schematic diagram illustrating a specific embodiment of the optical system 200 in accordance with the invention. In this embodiment, the first optics assembly 210 includes a beam conditioner 214 that produces a conditioned beam 212 including diffused and randomized radiation. The beam conditioner 214 can be a fiber optic line that transmits the beam from the irradiation source (not shown in FIG. 3) and an actuator that moves the fiber optic line to randomize the laser beam. The actuator can move the beam conditioner 214 in such a way that it does not repeat its movement over successive iterations to effectively randomize the radiation.

The beam conditioner 214 can further include or alternatively be an order sorter for removing undesired diffraction orders from the output. For example, the beam conditioner 214 may form a conditioned beam that provides a limited input to the object lens assembly 300 so that only a single, specific diffraction illuminates pre-selected parts of the detector. The beam conditioner 214 may include a carousel of apertures placed at the input of the optical system 200 so that different input apertures may be selected according to the desired diffraction order of the conditioned beam 212.

The first optics assembly 210 can further include a field stop 216 and an illumination lens 218. The field stop 216 is positioned in the first focal plane of the illumination lens 218, and the field stop 216 can have an aperture in a desired shape to influence the spot size and spot shape in conjunction with the illumination lens 218. In general, the illumination lens 218 collimates the radiation for presentation to the object lens assembly 300.

The embodiment of the object lens 300 illustrated in FIG. 3 can include a plurality of separate lenses. For example, the object lens assembly 300 can include a divergent lens 302, a first convergent lens 304, and a second convergent lens 306. The first convergent lens 304 can have a first maximum convergence angle, and the second convergent lens 306 can have a second maximum convergence angle (see FIG. 4). In operation, the object lens assembly 300 (a) focuses the conditioned beam 212 to form the convergent beam 310 and (b) presents the return radiation from the workpiece W on the second focal plane 340. The location of the second focal plane 340 depends upon the particular configurations of the lenses 302, 304 and 306. For purposes of illustration, the second focal plane 340 is shown as coinciding with the location of the first convergent lens 304.

The object lens assembly 300 is configured such that the angle $(\Theta_x, \Phi_y)$ of rays within the convergent beam 310 will pass through corresponding points (x, y) in the second focal plane 340. As a result, radiation passing through any given point (x, y) in the second focal plane 340 toward the workpiece W will pass through the object focal plane 320 at a particular corresponding angle $(\Theta_x, \Phi_y)$, and similarly radiation reflecting from the object focal plane 320 at a particular angle $(\Theta_x, \Phi_y)$ will pass through a unique point (x, y) on the second focal plane 340. The reflected radiation passing through the second focal plane 340 propagates to the beam splitter 220 where it is directed toward the second optics assembly 230.

The second optics assembly 230 includes a relay lens 232, an output beam splitter 234, and an image-forming lens 236. The relay lens 232 and output beam splitter 234 present the reflected and/or diffracted radiation (i.e., return radiation) from the beam splitter 220 to the image-forming lens 236, and the image-forming lens 236 "maps" the angular distribution of reflectance and/or diffraction (i.e., the radiation distribution) from the second focal plane 340 to the imaging array of the detector 400. In a particular embodiment, the image-forming lens 236 preferably presents the image to the detector 400 such that the pixels of the imager in the detector 400 can be mapped to corresponding areas in the second focal plane 340.

The second optics assembly 230 can further include a polarizing beam splitter 238 to separate the return radiation into the p- and s-polarized components. In one embodiment, the polarizing beam splitter 238 is positioned between the output beam splitter 234 and the image-forming lens 236. In another embodiment, the beam splitter 238 is positioned at a conjugate of the focal spot on the wafer along a path between the image-forming lens 236 and the detector 400 (shown in dashed lines). In still another embodiment, the polarizing beam splitter 238 can be located between the relay lens 232 and the output beam splitter 234 (shown in dotted lines). The polarizing beam splitter 238 is generally located to maintain or improve the spatial resolution of the original image of the focal spot on the workpiece. The location of the polarizing beam splitter 238 can also be selected to minimize the alteration to the original optical path. It is expected that the locations along the optical path between the relay lens 232 and the image-forming lens 236 will be the desired locations for the polarizing beam splitter 238.

The polarizing beam splitter 238 provides the separate p- and s-polarized components of the return radiation to improve the calibration of the scatterometer 10 and/or provide additional data for determining the parameter(s) of the microfeature on the workpiece. For example, because the optics may perturb the polarization of the input and output radiation, the polarizing beam splitter 238 provides the individual p- and s-polarized components over the large range of incidence angles. The individual p- and s-polarized components obtained in this system can accordingly be used to calibrate the scatterometer 10 to compensate for such perturbations caused by the optical elements. Additionally, the p- and s-polarized components can be used for obtaining additional data that can enhance the precision and accuracy of processing the data.

FIG. 3B is a schematic view of a cube-type polarizing beam splitter for use in the scatterometer 10 shown in FIGS. 2 and 3A. The cube-type polarizing beam splitter 238 receives a return radiation beam 239 and splits it into a p-polarized component beam 239a and an s-polarized component beam 239b. The cube-type polarizing beam splitter 238 can be a crystal with birefringence properties, such as calcite, KDP or quartz. The p- and s-polarized component beams 239a-b exit from the cube-type polarizing beam splitter 238 along at least substantially parallel paths. The p- and s-polarized beams 239a and 239b are also spaced apart from each other such that they form separate images on the detector 400. To increase the distance between the p- and s-polarized component beams 239a-b, the size of the polarizing beam splitter 238 can be increased. For example, as shown in dashed lines in FIG. 3B, a larger polarizing beam splitter 238 results in at least substantially parallel p- and s-polarized component beams 239a-b that are spaced apart from each another by a larger distance than the polarizing beam splitter 238 shown in solid lines 238. However, large cube-type polarizing beam splitters can alter the p- and s-polarized beams, and thus the size of polarizing beam splitter 238 is generally limited. As with the non-polarized return radiation, the individual p- and s-polarized component beams 239a-b impinge upon pixels of the detector 400 in a manner that they can be mapped to corresponding areas in the second focal plane 340 shown in FIG. 3A.

One advantage of several embodiments of scatterometers including cube-type polarizing beam splitters it that they provide fast, high-precision measurements of the p- and s-polarized components with good accuracy. The system illustrated in FIGS. 3A-B use a single camera in the detector 400 to simultaneously measure both of the p- and s-polarized components of the return radiation 239. This system eliminates the problems of properly calibrating two separate cameras and registering the images from two separate cameras to process the data from the p- and s-polarized components. This system also eliminates the problems associated with serially polarizing the return radiation beam using a mechanically operated device because the polarizing beam splitter 238 can be fixed relative to the return beam 239 and the detector 400.

Another aspect of several embodiments of the optics is that a sine relationship or another suitable relationship is maintained between the pixels on the image sensor and the altitude angles of the beam. This allows a linear relationship between pixels on the image sensor and altitude angles. As such, the optics enable good sampling of the return radiation even at the peripheral regions of an image sensor.

D. Embodiments of Detectors

The detector 400 can have several different embodiments depending upon the particular application. In general, the detector is a two-dimensional array of sensors, such as a CCD array, a CMOS imager array, or another suitable type of "camera" or energy sensor that can measure the intensity, color or other property of the scattered radiation from the workpiece W corresponding to the distribution at the second focal plane 340. The detector 400 is preferably a CMOS imager because it is possible to read data from only selected pixels with high repeatability instead of having to read data from an entire frame. This enables localized or selected data reading, which is expected to (a) reduce the amount of data that needs to be processed and (b) eliminate data that does not have a meaningful contrast. Additional aspects of using CMOS images for image processing are described in more detail below. The p- or s-polarized components can be measured with a single CMOS imager to determine certain characteristics that are otherwise undetectable from non-polarized light. As such, using a CMOS imager and polarizing the reflected radiation can optimize the response to increase the resolution and accuracy of the scatterometer 10.

FIG. 3C is a schematic view showing a CMOS imager assembly for use in the detector 400 in accordance with an embodiment of the invention. In this example, the CMOS imager assembly includes a die 410 having an image sensor 412, focal optics 420, and packaging 430 defining an enclosed compartment 432 between the die 410 and the focal optics 420. The focal optics 420 typically have curved surfaces or other configurations such that they are not merely a plate having parallel, flat surfaces. Additionally, the CMOS imager assembly does not have a glass cover or other optical member with parallel, flat surfaces between the image sensor 412 and the focal optics 420. As such, the CMOS imager assembly illustrated in FIG. 3C does not have any flat optics in the compartment 432 between the image sensor 412 and the focal optics 420. In this embodiment, the polarizing beam splitter 238 is just upstream of the CMOS imager assembly 400 relative to the return radiation beam 239.

The CMOS imager assembly 400 illustrated in FIG. 3C is expected to provide several advantages for use in scatterometers. In several embodiments, for example, the lack of a cover or other flat optical member between the image sensor 412 and the focal optics 420 is expected to reduce perturbations in the return radiation beam 239 at the image sensor 412. More specifically, a glass member with parallel, flat surfaces between the focal optics 420 and the image sensor 412 can alter the return radiation just before it reaches the image sensor 412. By eliminating such glass members with parallel, flat surfaces, the CMOS imager assembly illustrated in FIG. 3C is expected to eliminate distortion or interference caused by a glass member with parallel surfaces.

E. Navigation and Auto-Focus Systems

Referring back to FIG. 1, the navigation system 500 accurately aligns the beam 310 with a desired area on the workpiece W, and the auto-focus system 600 adjusts the object lens assembly 300 or workpiece site 510 so that the object focal plane 320 is at the microstructure. In one embodiment, the navigation system 500 has a separate illumination source, lens and measurement optics for determining the precise location of the microstructure on the workpiece W. The light source of the navigation system 500 can be a LED, and the lens and optics can be a two-stage system having low and high magnifications. The low magnification stage identifies the general area on the wafer where the microstructure is located, and the high magnification stage refines the location. In other embodiments, the navigation system 500 can include additional relay optics introduced to image the surface directly through the object lens assembly 300.

The auto-focus system 600 can be a camera correlation focus system having a dihedral mirror that simultaneously splits the illumination pupil in two and redirects the light from the two halves of the dihedral mirror to different sections of a CCD array. The displacement between the two images is used to automatically determine the focus. A field stop can be incorporated to prevent overlap of the two images on the focus camera. The field stop is included in the illumination beam of the microscope of the auto-focus system.

Figure 4:
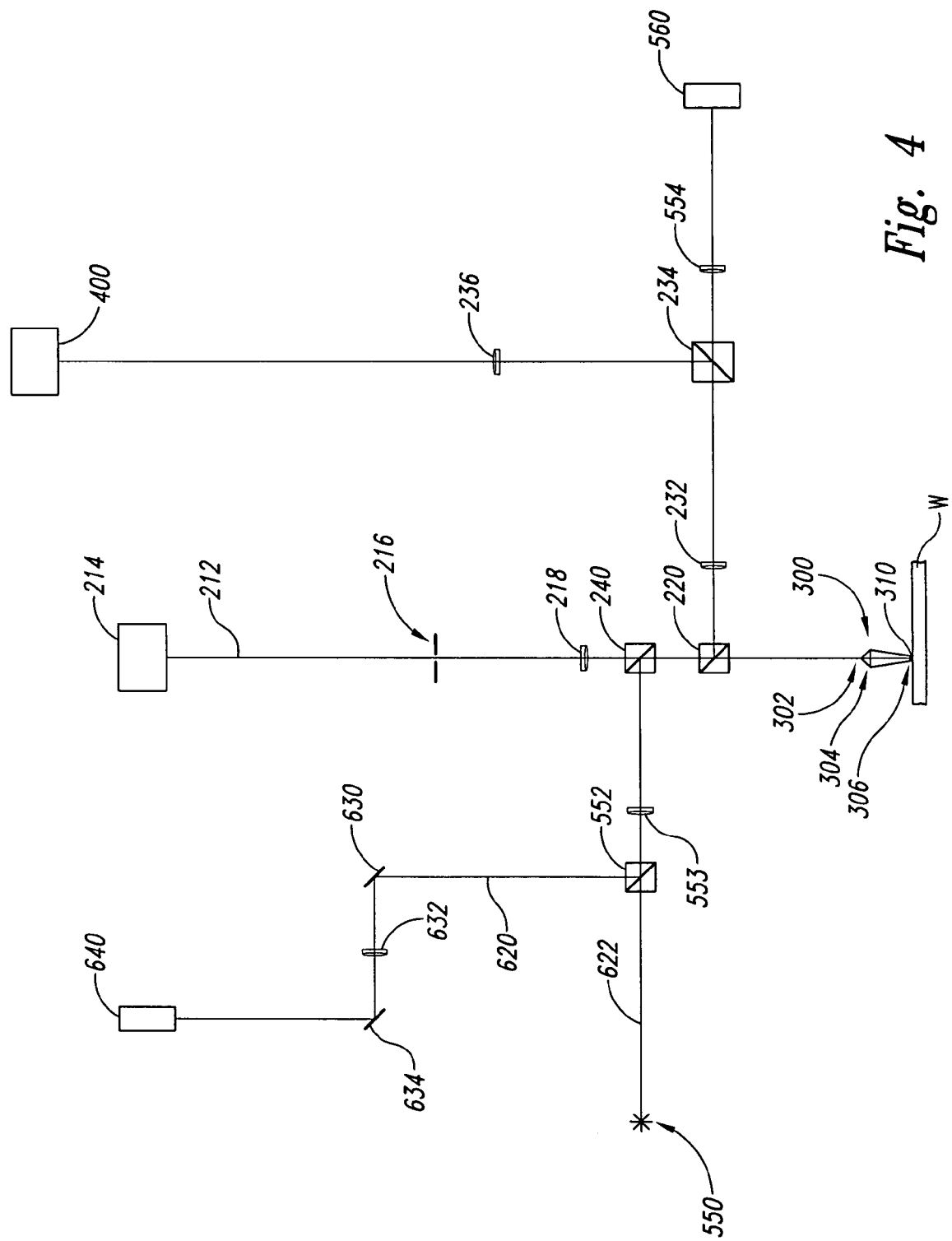
FIG. 4 is a schematic view illustrating an optical system and an auto-focus system for use in a scatterometer in accordance with an embodiment of the invention.

FIG. 4 is a schematic illustration of an embodiment of the navigation system 500 and auto-focus system 600 for use in the scatterometer. Several aspects of FIG. 4 are similar to those explained above with reference to FIGS. 1 and 3A, and thus like reference numbers refer to like components in these figures. The navigation system 500 can have a high magnification system associated with the metrology system. For example, the high magnification system includes a light source 550, such as an LED, that injects light via a beam splitter 552 and is focused on the second focal plane by a relay lens 553 via beam splitter 240. This light illuminates the workpiece and is reflected back through the object lens assembly 300. The reflected light is directed by beam splitter 220 and through lenses 232 and 554 to camera 560. The lenses 232 and 554 form an image of the microstructure on the camera 560.

The auto-focus system 600 in this embodiment shares the relay lens 553 and the beam splitter 552 with the navigation system. The beam splitter 552 directs a beam 620 to a dihedral mirror 630, an image lens 632, and a steering mirror 634. The first beam 620 is then received by an auto-focus detector 640, such as a CCD array or other type of camera.

F. Calibration

The calibration system is used to monitor the properties of the initial beam 102 (FIG. 1) and calibrate the system efficiency for accurately detecting the radiation distribution. The beam properties are monitored by a reference detector 700 that receives a portion of the beam 102 in real time. As the beam fluctuates, the reference detector 700 detects the changes in the beam 102 and sends a signal to the computer 800. The computer 800 accordingly normalizes and/or performs other computational operations to the measured intensities, or it adjusts the measured radiation distribution by the variances in the intensity of the initial beam 102, to compensate for small changes in the beam 102. Unlike some systems that do this periodically, the computer 800 continuously receives signals from the reference detector 700 to maintain the accuracy of the system in real time. This is expected to significantly enhance the accuracy and precision with which the scatterometer 10 can evaluate extremely small features in microstructures.

The calibration system can also include a calibration unit, such as the calibration unit 704 (FIG. 1) with one or more calibration members, for providing photometric calibration of the system. In one embodiment, the first calibration member 710 can be a highly reflective mirror having a reflectance greater than 95%, and more preferably a reflectance of approximately 99.99%. The first calibration member 710 can be configured to have a consistent reflectance through a wide range of altitude angles. The second calibration member 720 can be black glass having a low reflectance (e.g., 0% to 10%). In operation, the detector 400 is calibrated by measuring the reflectance of the beam from the first calibration member 710 and from the second calibration member 720 to provide two data points corresponding to the known 99.99% reflectance of the first calibration member 710 and the known 0% reflectance of the second calibration member 720. Using these two data points, a straight line can be obtained to provide a reference reflectance of the detector 400.

In another embodiment of the calibration unit 704, the second calibration member 720 is not included or the second calibration member can be free space such that there is no reflectance of the illumination radiation. In this embodiment, the scatterometer 10 is calibrated by obtaining a first reflectivity from the first calibration member 710 and a second reflectivity from an area separate from the first calibration member 710. When the second reflectivity is obtained from free space, there is approximately zero percent reflectance such that a straight line can be obtained from these two measurements to provide a reference reflectance of the detector 400.

The scatterometer can be calibrated further using several different methods. For example, a known grating with a known radiation distribution can be measured using the scatterometer 10 to determine whether the detector 400 accurately produces a representation of the radiation distribution. In another embodiment, a thin film having a known thickness can be irradiated to determine whether the detector 400 provides an accurate representation of the radiation distribution from such a thin film. Both of these techniques can also be combined for yet another calibration method.

G. Computational Analyses

The computer 800 can use several different processes for determining one or more parameters of the microstructure based on the measured radiation distribution from the detector 400. In general, the computer 800 compares the measured radiation distribution with one or more simulated radiation distributions corresponding to selected parameters of the features and materials of the microstructure (e.g., height, width, line edge roughness, roundness of edge corners, spacing, film thickness, refraction index, reflection index, and/or other physical properties). Based on the comparison, the computer 800 then stores and/or provides an output of one or more parameters of the microstructure.

Figure 5A:
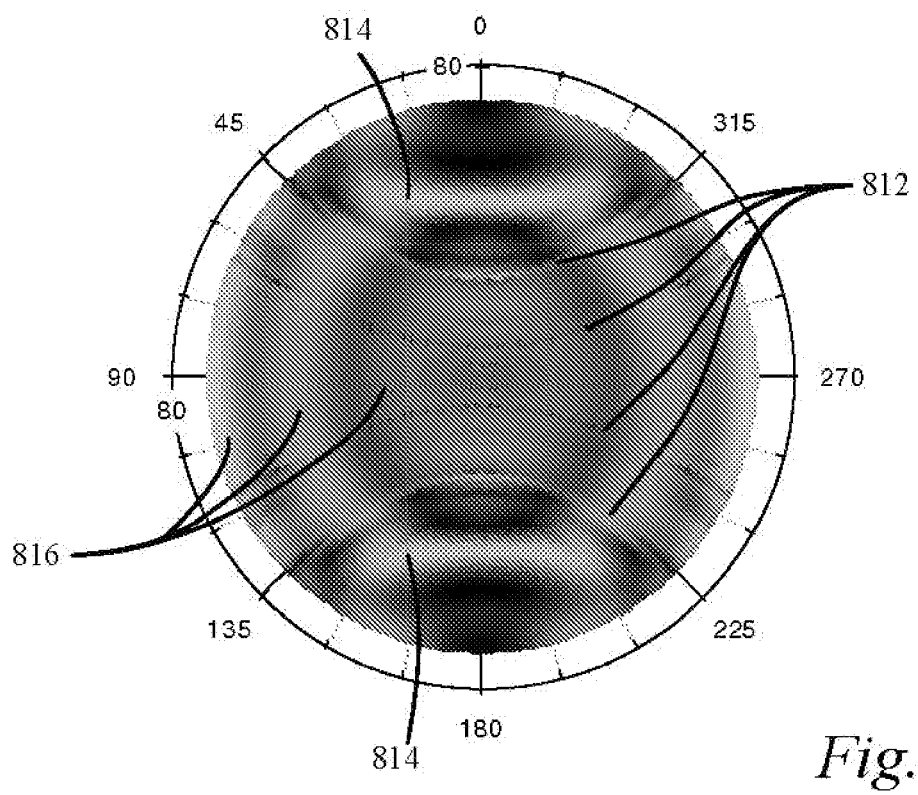
FIG. 5A is a simulated radiation distribution for use in a scatterometer in accordance with an embodiment of the invention.

FIG. 5A is an image illustrating a simulated radiation distribution 810 having a first interference pattern 812 including a plurality of thin arcs, a second interference pattern 814 including a plurality of different arcs, and a third interference pattern 816 in a configuration of a "bulls-eye." The first interference pattern 812 can correspond to the specular reflections, the second interference pattern 814 can correspond to higher order diffractions, and the third interference pattern 816 can correspond to the film thickness. The symmetry of the image can also be assessed to provide additional information regarding the microstructure. For example, in overlay applications, asymmetry in the image can be used to evaluate the skew between overlay structures (e.g., the extent of misregistration). Another example of using the image symmetry is determining the asymmetry of sidewall angles of grating lines. The interference patterns of the simulated radiation distribution 810 are unique to each set of feature parameters, and thus changing one or more of the feature parameters will produce a different simulated radiation distribution.

Figure 5B:
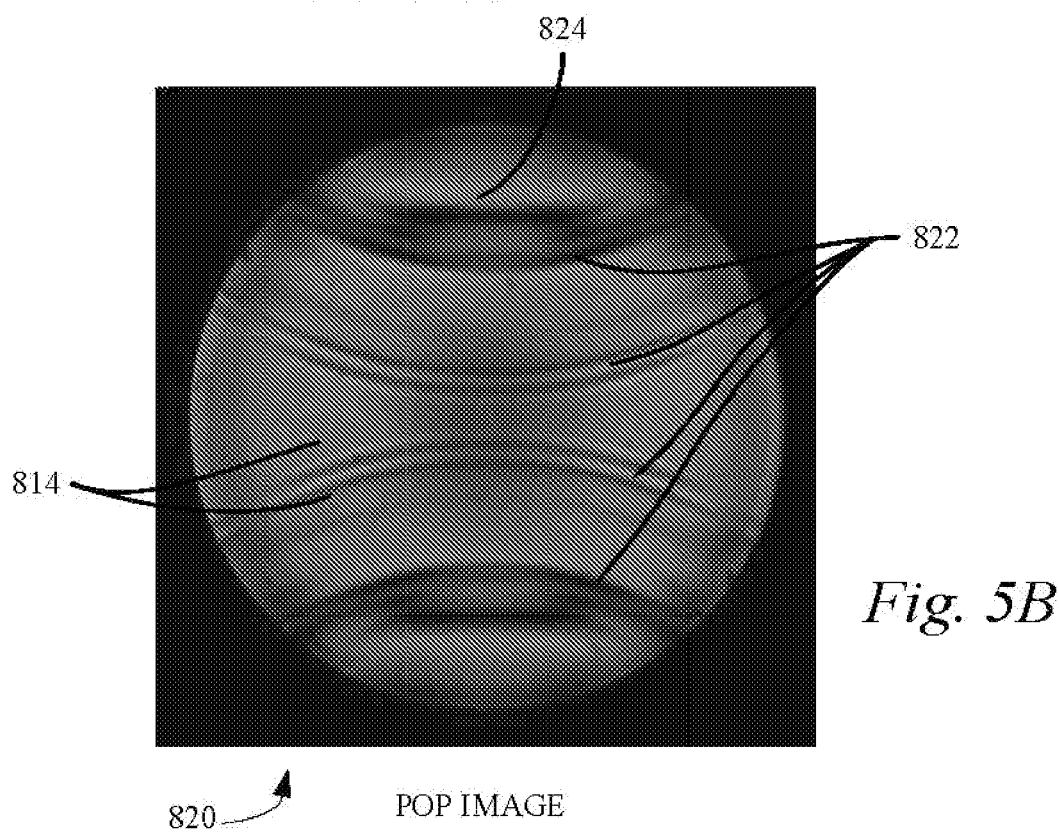
FIG. 5B is a measured radiation distribution provide by a scatterometer in accordance with an embodiment of the invention.

FIG. 5B is an image of a measured radiation distribution 820 of an actual microstructure on a workpiece. The measured radiation distribution 820 includes a corresponding first interference pattern 822, a second interference pattern 824, and a third interference pattern 826. In operation, the computer 800 ascertains the parameters of the microstructure by selecting and/or determining a simulated radiation distribution 810 that best fits the measured radiation distribution 820.

Figure 6:
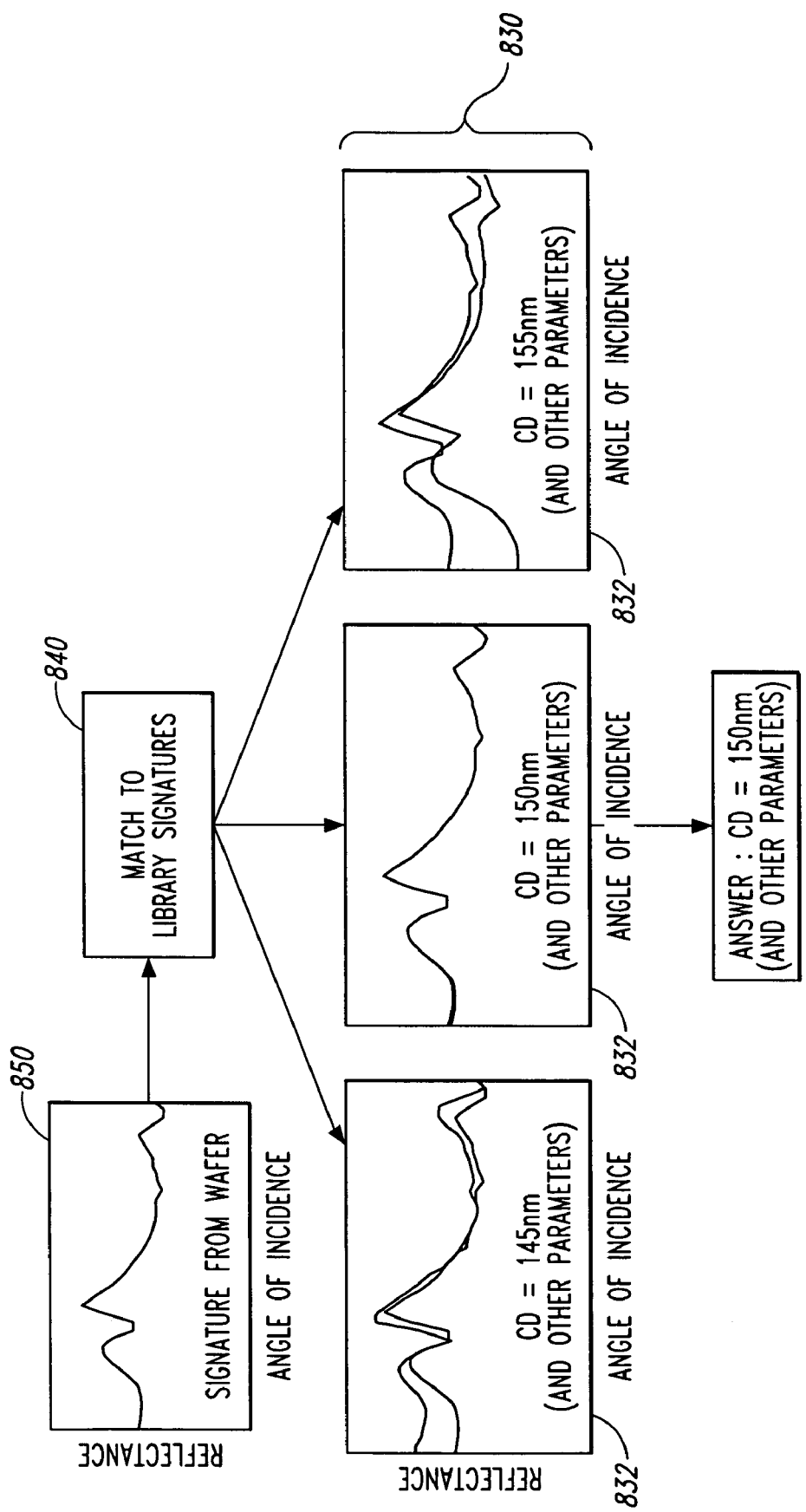
FIG. 6 is a schematic view illustrating a portion of a computer system and a computational method for ascertaining parameters of microstructures using a scatterometer in accordance with an embodiment of the invention.

FIG. 6 illustrates one embodiment for ascertaining the feature parameters of the microstructure. In this embodiment, the computer 800 includes a database 830 including a large number of predetermined simulated reference radiation distributions 832 corresponding to different sets of feature parameters. The computer 800 further includes a computer-operable medium 840 that contains instructions that cause the computer 800 to select a simulated radiation distribution 832 from the database 830 that adequately fits a measured radiation distribution 850 within a desired tolerance. The computer-operable medium 840 can be software and/or hardware that evaluates the fit between the stored simulated radiation distributions 832 and the measured radiation distribution 850 in a manner that quickly selects the simulated radiation distribution 832 having the best fit with the measured radiation distribution 850 or at least having an adequate fit within a predetermined tolerance. In the case where a plurality of the simulated radiation distributions 832 have an adequate fit with the measured radiation distribution 850, the computer 800 can extrapolate or interpolate between the simulated distributions. Once the computer has selected a simulated radiation distribution with an adequate fit or the best fit, the computer selects the feature parameters associated with the selected simulated distribution.

In an alternative embodiment, the computer calculates a simulated radiation distribution and performs a regression optimization to best fit the measured radiation distribution with the simulated radiation distribution in real time. Although such regressions are widely used, they are time consuming and they may not reach a desired result because the regression may not converge to within a desired tolerance.

In still other embodiments, the computer 800 may perform further processing or different processing such as finite element models for evaluating non-periodic or pseudo-periodic structures. The computer 800 may also be able to solve for the refraction index and reflectivity index of the particular materials by determining the film thickness. Therefore, the enhanced data in the measured radiation distribution enables the computer 800 to more accurately determine the feature parameters of the microstructure and may enable more feature structures to be monitored (e.g., line edge roughness, refraction index, reflectivity index, etc.).

Figure 7:
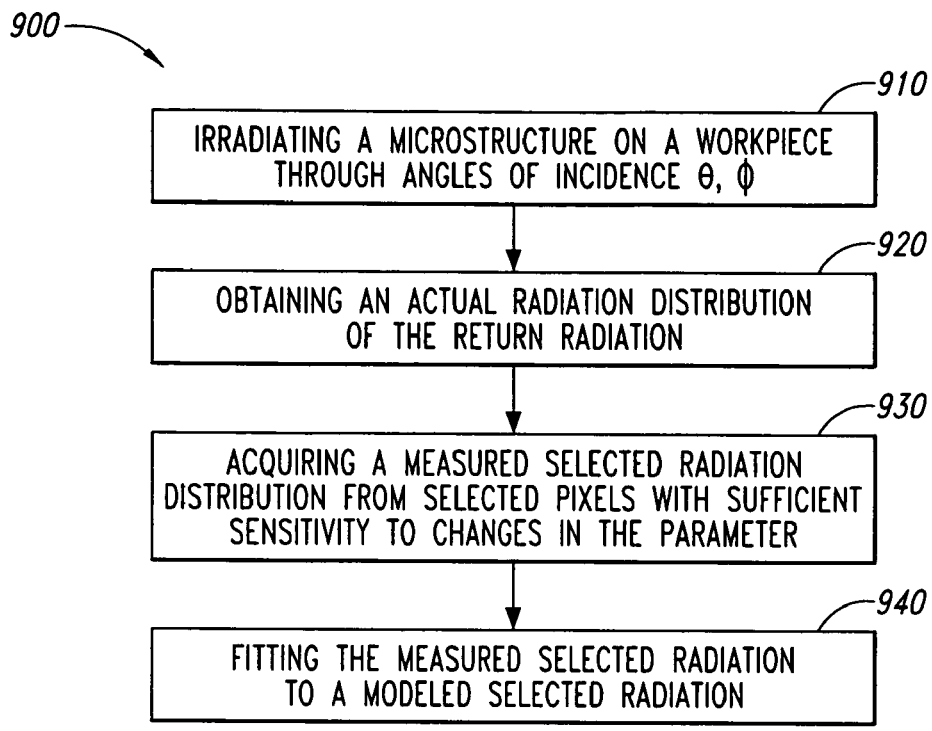
FIG. 7 is a flow chart illustrating a method for determining one or more parameters of a microfeature using a scatterometer in accordance with an embodiment of the invention.

FIG. 7 is a flow chart showing a method 900 for ascertaining one or more parameters of a microstructure using the computer 800 in accordance with another embodiment of the invention. In this embodiment, the method 900 includes a first stage 910 comprising irradiating a microstructure on a workpiece by passing a beam through an object lens assembly that simultaneously focuses the beam to a focus area at an object plane through a large number of incidence angles. The beam for example, can be focused simultaneously through angles of incidence having altitude angles of 0° to at least 45° and azimuth angles of 0° to greater than 90°. The method 900 further includes a second stage 920 comprising obtaining an actual radiation distribution of scattered light or other radiation returning from the microstructure through the angles of incidence. The actual radiation distribution can be obtained using an array of addressable pixels that can be scanned or read individually. The method 900 further includes a third stage 930 comprising acquiring a measured selected radiation distribution by reading data from selected pixels in the array that have sufficient sensitivity to changes in the parameter based upon a predetermined sensitivity record, and a forth stage 940 comprising fitting the measured selected radiation distribution to simulated or modeled selected radiation distributions corresponding to the selected pixels to determine a value of the parameter. The method 900 is expected to be particularly useful because selected areas of the pixel array with high sensitivity to changes in the measured parameter can be scanned, and then this smaller amount of data that is more sensitive to changes in the measured parameter can be fitted to modeled distributions.

The first stage 910 of the method 900 can be performed using a scatterometer as described and shown above with reference to FIGS. 1-4. As such, an input beam can be passed through an object lens assembly that forms a beam having a large range of incident angles ($\Theta$, $\Phi$) to capture a significant amount of data in a single measurement of the workpiece. The altitude angles $\Phi$ can be from 0° to approximately 80° to 88° and the azimuth angles $\Theta$ can be from 0° to 360° as explained above.

After irradiating the microstructure, the second stage 920 of the method 900 can include obtaining the actual radiation distribution of radiation returning from the microstructure through the same angles of incidence as described above with reference to the detector 400. In this embodiment, the detector is preferably a CMOS imager that has an array of addressable pixels in which individual pixels can be independently scanned.

The third stage 930 of the method 900 comprises scanning or otherwise acquiring the actual intensity measurements from selected pixels of the array corresponding to angles of incidence that are highly sensitive to changes in the measured parameter(s) based upon a predetermined sensitivity record. The sensitivity record can be a pixel-by-pixel analysis of a plurality of pixels in the array that correspond to individual incidence angles ($\Phi_n$, $\Theta_n$). At each pixel, model intensities of the return radiation are calculated for different values of the parameter, and then the model intensities are subtracted from each other to determine the magnitudes of the changes in the intensity for the incremental changes in the parameter. Larger intensity changes correspond to pixels and angles of incidence that are more sensitive to changes in the parameter compared to smaller changes in the intensity.

Figure 8:
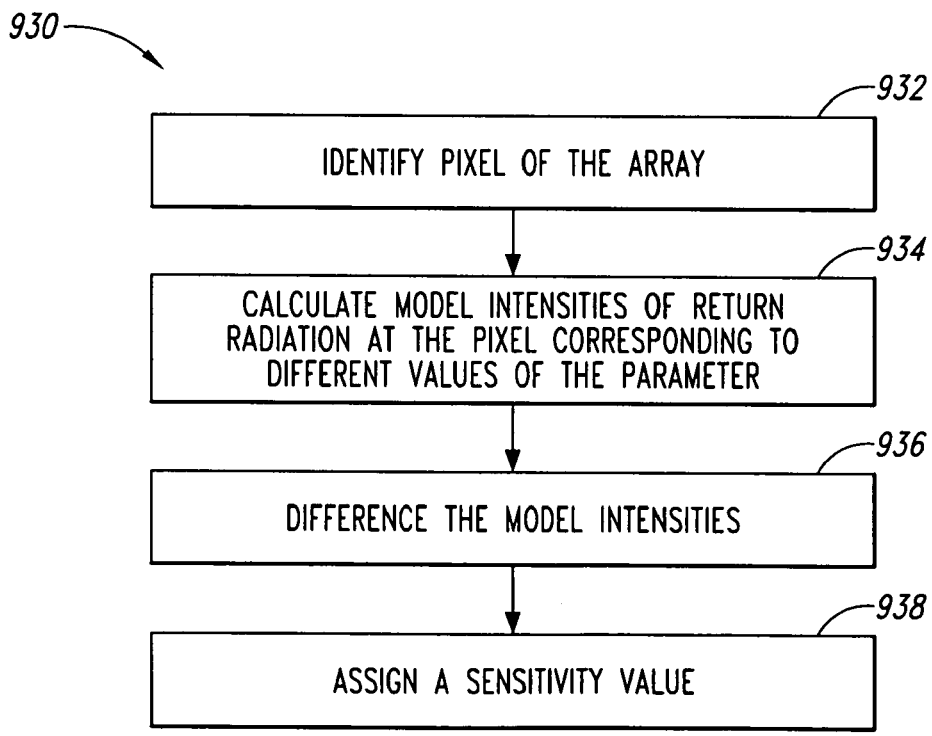
FIG. 8 is a flow chart of a procedure for developing a predetermined sensitivity record used in a method for assessing a parameter of a microfeature on a workpiece in accordance with an embodiment of the invention.

FIG. 8 is a flow chart illustrating an embodiment of the third stage 930 for use in the method 900. In this embodiment, the third stage 930 includes identifying a pixel of the array (procedure 932), and then calculating model intensities of the return radiation at the pixel that correspond to different values of the parameter (procedure 934). This embodiment of the third stage 930 further includes differencing the model intensities (procedure 936) to determine the magnitude of change in the intensities corresponding to changes in the parameter. Based upon the magnitudes of the changes in the model intensities determined in procedure 936, the third stage 930 further includes assigning a sensitivity value (procedure 938) to a corresponding pixel. A third stage 930 can be repeated for any number of pixels in a CMOS imager array to develop a predetermined sensitivity record that associates the pixels in the array with the sensitivity to changes in the parameter.

FIGS. 9A and 9B graphically illustrate an embodiment of developing a predetermined sensitivity record for a parameter and selecting pixels in the array that have sufficient sensitivity to changes in the parameter for use in the measured selected radiation distribution. FIG. 9A, more specifically, shows model intensity distributions for three different values of a parameter (e.g., the critical dimension) through angles of incidence where $\Theta$ is from 0° to approximately 65° and $\Phi$ is from 0° to approximately 90°. In FIG. 9A, the intensity distribution 952 corresponds to a first value of the parameter, the intensity distribution 954 corresponds to a second value of the parameter, and the intensity distribution 956 corresponds to a third value of the parameter. Although the data in the intensity distributions 952, 954 and 956 is useful, it does not provide an indication of which incidence angles (e.g., pixels in a CMOS imager) are more sensitive to changes in the parameter. FIG. 9B is a sensitivity map 960 illustrating a sensitivity record associating the sensitivity of various incidence angles to changes in the parameter. The sensitivity map is obtained by differencing the model intensities at corresponding incidence angles between the intensity distributions 952, 954 and 956 shown in FIG. 9A. The sensitivity map 960 shown in FIG. 9B assigns a sensitivity value according to the magnitude of the difference between the model intensity distributions. In this embodiment, bright regions indicate angles of incidence that are more sensitive to changes in the parameter and dark regions indicate angles of incidence that are less sensitive to changes in the parameter. The sensitivity values for the angles of incidence can then be associated with the pixels in the CMOS imager array corresponding to the angles of incidence.

One aspect of the method 900 is that the sensitivity map 960, which is a graphical representation of the sensitivity record, provides an indication of the angles of incidence that may provide the most valuable data corresponding to changes in the parameter. Additionally, because specific pixels of a CMOS imager can be scanned or read individually, one aspect of the method 900 is determining which pixels in the CMOS imager array have high sensitivities from which the measured intensity values can be acquired (e.g., scanned).

FIG. 9C illustrates one embodiment of selecting pixels in the array that have sufficient sensitivity to changes in the parameter based upon the predetermined sensitivity record or sensitivity map. Referring to FIG. 9C, pixels in the CMOS imager array corresponding to angles of incidence in the bright region 962 are expected to provide good data because this area indicates a region of high sensitivity, and pixels associated with angles of incidence in the dark region 964 are likely to have low sensitivity to changes in the parameter. As such, the measured selected radiation distribution can be acquired by reading data from the pixels in the array corresponding to angles of incidence that have a high sensitivity to changes in the parameter based on the predetermined sensitivity record. After scanning the pixels that correspond to angles of incidence which have a high sensitivity, the measured selected radiation distribution from such pixels is compared to modeled radiation distributions from the same angles of incidence until the measured selected radiation distribution adequately fits with one of the modeled selected radiation distributions. At this point, a value of the parameter is determined according to the corresponding best fit of the modeled selected radiation distribution.

The method 900 can be applied to applications in which several parameters of the microfeature are to be assessed using scatterometry. In such multi-parameter applications, separate sensitivity records are established for individual parameters by varying the parameter of interest while keeping the other parameters constant. The regions of the CMOS imager array that are scanned can then be determined by selecting the sets of pixels corresponding to high sensitivity values for the parameters that are to be assessed using the scatterometer.

In practice, the sensitivity record can be used to optimize the scan path to retrieve data from only the pixels that have sufficient sensitivity, and to also fit the data from the selected pixels to corresponding models in a library. This is expected to significantly reduce the simulation times for arriving at a value of one or more parameters because it reduces the number of ($\Theta$, $\Phi$) combinations that need to be stored in a library and used to fit the measured selected radiation distribution to a modeled selected radiation distribution. The system is also expected to increase the acquisition rate because only a portion of the pixels in the CMOS imager need to be scanned for each measurement. This provides more measurements in a given exposure period, which can lead to better averaging and lower signal-to-noise ratios. This method is also expected to enhance the precision (e.g., repeatability) because it uses only data from highly sensitive pixels. Additionally, this method is useful because it is possible to overlay known pixel noise for a particular CMOS imager array with the sensitivity array such that pixels with high sensitivities caused by noise can be eliminated from the measurements. Therefore, such an image fitting procedure that scans only selected pixels of a CMOS imager array with high sensitivity values is expected to significantly improve the computational analysis for determining values of parameters in scatterometry.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A scatterometer for evaluating a microstructure on a workpiece, comprising:
   an irradiation system configured to produce a first beam of radiation having a first wavelength and a second beam of radiation having a second wavelength;
   an optical system having a first optics assembly configured to condition the first and second beams, and an object lens assembly configured to (a) individually focus the first and second beams to an area at an object focal plane through at least a 150° range of altitude angles and at least a 900° range of azimuth angles simultaneously, and (b) present return radiation scattered from a microstructure in a radiation distribution at a second focal plane;
   a detector having a two-dimensional sensor array positioned to receive the radiation distribution and configured to produce a representation of the radiation distribution on the two-dimensional sensor array; and
   a computer system operatively coupled to the detector and including a computer operable medium, wherein the computer operable medium includes instructions that cause the computer system to acquire a measured selected radiation distribution by reading data from selected pixels of the two-dimensional sensor array, the selected pixels being less than the total number of illuminated pixels in the two-dimensional sensor array.

2. The scatterometer of claim 1, further comprising a navigation system having a light source separate from the irradiation source and navigation optics having a low magnification capability for locating a general area of the microstructure and a high magnification capability for accurately aligning the object lens with the microstructure.

3. The scatterometer of claim 1 wherein the object lens assembly is configured to focus the conditioned beam to a spot size not greater than 30 μm.

4. The scatterometer of claim 1 wherein the irradiation source comprises a laser and/or a lamp configured to generate the first beam having a first wavelength and the second beam having a second wavelength different than the first wavelength.

5. The scatterometer of claim 4 wherein the first wavelength is approximately 266 nm and the second wavelength is approximately 405 nm.

6. The scatterometer of claim 1 wherein the first wavelength is approximately 200 nm to approximately 475 nm.

7. The scatterometer of claim 1 wherein the first wavelength is approximately 375 nm to approximately 475 nm.

8. The scatterometer of claim 4 wherein the first wavelength is approximately 244 nm and the second wavelength is 457 nm.

9. The scatterometer of claim 1 wherein the first wavelength is one of approximately 405 nm or 457 nm.

10. The scatterometer of claim 1, wherein the computer system includes a database having a plurality of simulated radiation distributions corresponding to different sets of parameters of the microstructure and the computer-operable medium further contains instructions that cause the computer system to identify a simulated radiation distributions that adequately fits to the representation of the radiation distribution produced by the detector.

11. The scatterometer of claim 1, further comprising:
a calibration member having a first reflectivity of the first wavelength located proximate to a workpiece site; and
wherein the computer-operable medium further contains instructions that determine a reference reflectance using a first detected reflectance from the first calibration member and a second detected reflectance from an area separate from the calibration member.

12. The scatterometer of claim 11 wherein the calibration member comprises a mirror having a reflectance greater than approximately 95% and capable of reflecting radiation through a range of altitude angles of 0° to 89°, and the second reflectance is from free space.

13. The scatterometer of claim 1 wherein the first optics assembly comprises a diffuser that produces a diffuse randomized beam.

14. The scatterometer of claim 1 wherein the first optics assembly comprises an order selector configured to limit the angular range of various diffraction orders.

15. The scatterometer of claim 1 wherein the first optics assembly is configured to diffuse and randomize the beam; and
the scatterometer further comprises a field stop having an aperture and an illumination lens through which the diffused and randomized beam pass.

16. The scatterometer of claim 1 wherein the object lens assembly comprises a plurality of achromatic lenses.

17. The scatterometer of claim 1, further comprising a plurality of optical heads, wherein individual optical heads are suitable for a unique bandwidth of radiation.

18. The scatterometer of claim 1, further comprising a reference detector configured to measure changes in the beam from the irradiation source.

19. The scatterometer of claim 1 wherein the object lens assembly is further configured to simultaneously focus the conditioned beam at the object focal plane through a range of incidence angles having (a) altitude angles of 0° to at least about 45° and (b) azimuth angles of 0° to at least about 90°.

20. The scatterometer of claim 19 wherein the altitude angles are 0° to at least 70° and the azimuth angles are 0° to at least 180°.

21. The scatterometer of claim 19 wherein the altitude angles are 0° to at least 80° and the azimuth angles are 0° to at least 360°.

22. The scatterometer of claim 1, further comprising a polarizing beam splitter in a path of the return radiation between the object lens assembly and the detector to separate the p- and s-polarized components of the return radiation from each other.

23. The scatterometer of claim 22, further comprising a single detector to receive both the p- and s-polarized components of the return radiation, and wherein the polarizing beam splitter comprises a cube-type polarizing beam splitter.

24. The scatterometer of claim 1, wherein the computer system includes a database that includes a sensitivity record of sensitivity to changes in the parameter at pixels in the array, and wherein the computer operable medium includes instructions that cause the computer system to acquire the measured selected radiation distribution by reading data from selected pixels of the array based on pixels having sufficient sensitivity to changes in the parameter using the sensitivity record, and fit the measured selected radiation distribution to a modeled selected radiation distribution corresponding to the selected pixels to determine a value of the parameter.

25. The scatterometer of claim 24 wherein the computer operable medium further comprises instructions that cause the computer system to determine the sensitivity record by:
identifying a pixel of the array associated with an incident angle;
calculating model intensities of return radiation at the pixel corresponding to different values of the parameter;
differentiating the model intensities, wherein larger differences in the model intensities indicate higher sensitivity to changes in the parameter and smaller differences in the model intensities indicate lower sensitivity to changes in the parameter at the selected pixel; and
assigning a sensitivity value to the pixel.

26. The scatterometer of claim 25 wherein the computer operable medium further comprises instructions that cause the computer system to repeat the identifying, calculating, differentiating and assigning procedures for additional pixels in the array such that the sensitivity record includes sensitivity values for a plurality of pixels.

27. The scatterometer of claim 26 wherein the computer operable medium includes instructions that cause the computer system to acquire the measured selected radiation distribution by selecting pixels having sensitivity values above a threshold value.

28. A scatterometer for evaluating a microstructure on a workpiece, comprising:
a light source that produces a beam of radiation having at least one wavelength;
an optical system having an object lens assembly configured to (a) focus the beam of radiation to an area at an object focal plane through at least a 15° range of altitude angles and at least a 90° range of azimuth angles simultaneously, and (b) present return radiation scattered from a microstructure in a radiation distribution;
a detector having a two-dimensional sensor array positioned to receive the radiation distribution and configured to produce an image of the radiation distribution on the two-dimensional sensor array; and a computer operatively coupled to the detector and including a computer operable medium, wherein the computer operable medium includes instructions that cause the computer to acquire a measured selected radiation distribution by reading data from selected pixels of the two-dimensional sensor array, the selected pixels being less than the total number of illuminated pixels in the two-dimensional sensor array.

29. The scatterometer of claim 28, wherein the optical system further has an optics assembly configured to condition the beam of radiation.

30. The scatterometer of claim 28 wherein the optics assembly comprises at least one of a diffuser that produces a diffuse randomized beam and an order selector configured to limit the angular range of various diffraction orders.

31. The scatterometer of claim 28, further comprising a polarizing beam splitter in a path of the return radiation between the object lens assembly and the detector to separate the p- and s-polarized components of the return radiation from each other.

32. The scatterometer of claim 31, wherein the detector having the two-dimensional sensor array receives both the p- and s-polarized components of the return radiation, and wherein the polarizing beam splitter comprises a cube-type polarizing beam splitter.

33. The scatterometer of claim 28, wherein the computer includes a database that includes a sensitivity record of sensitivity to changes in the parameter at pixels in the array, and wherein the computer operable medium includes instructions that cause the computer to acquire the measured selected radiation distribution by reading data from selected pixels of the array based on pixels having sufficient sensitivity to changes in the parameter using the sensitivity record, and fit the measured selected radiation distribution to a modeled selected radiation distribution corresponding to the selected pixels to determine a value of the parameter.

34. A scatterometer for evaluating a microstructure on a workpiece, comprising:

a light source that produces a beam of radiation having at least one wavelength;

an optical system having an object lens assembly configured to (a) focus the beam of radiation to an area on a microstructure, and (b) present return radiation scattered from the microstructure in a radiation distribution;

a detector having a two-dimensional sensor array positioned to image the radiation distribution and configured to produce a representation of the radiation distribution on the two-dimensional sensor array; and a computer system operatively coupled to the detector and including a computer operable medium, wherein the computer operable medium includes instructions that cause the computer system to acquire a measured selected radiation distribution by reading data from selected pixels of the two-dimensional sensor array, the selected pixels being less than the total number of illuminated pixels in the two-dimensional sensor array.

* * * * *